US008957034B2

(12) United States Patent
Hanes et al.

(10) Patent No.: US 8,957,034 B2
(45) Date of Patent: Feb. 17, 2015

(54) DRUGS AND GENE CARRIER PARTICLES THAT RAPIDLY MOVE THROUGH MUCOUS BARRIERS

(75) Inventors: Justin Hanes, Baltimore, MD (US); Michelle Rose Dawson, Arlington, MA (US); Denis Wirtz, Washington, DC (US); Jie Fu, Baltimore, MD (US); Eric Mark Krauland, Somerville, MA (US)

(73) Assignee: Johns Hopkins University, Baltimore, MD (US)

( * ) Notice: Subject to any disclaimer, the term of this patent is extended or adjusted under 35 U.S.C. 154(b) by 1263 days.

(21) Appl. No.: 10/587,512

(22) PCT Filed: Jan. 28, 2005

(86) PCT No.: PCT/US2005/002556
§ 371 (c)(1),
(2), (4) Date: Nov. 8, 2007

(87) PCT Pub. No.: WO2005/072710
PCT Pub. Date: Aug. 11, 2005

(65) Prior Publication Data
US 2008/0166414 A1    Jul. 10, 2008

Related U.S. Application Data

(60) Provisional application No. 60/539,773, filed on Jan. 28, 2004, provisional application No. 60/579,533, filed on Jun. 14, 2004.

(51) Int. Cl.
*A61K 48/00* (2006.01)
*A61K 9/51* (2006.01)
*A61K 9/00* (2006.01)
*A61K 9/16* (2006.01)
*A61K 9/50* (2006.01)
*A61K 47/48* (2006.01)
*B82Y 5/00* (2011.01)

(52) U.S. Cl.
CPC ............. *A61K 9/5123* (2013.01); *A61K 9/0073* (2013.01); *A61K 9/167* (2013.01); *A61K 9/5031* (2013.01); *A61K 9/5153* (2013.01); *A61K 47/48046* (2013.01); *A61K 47/48907* (2013.01); *A61K 47/48915* (2013.01); *B82Y 5/00* (2013.01)
USPC ...................................... 514/44 R

(58) Field of Classification Search
USPC .......................................... 514/44
See application file for complete search history.

(56) References Cited

U.S. PATENT DOCUMENTS

| 4,757,128 A | 7/1988 | Domb et al. |
| 4,789,724 A | 12/1988 | Domb et al. |
| 4,792,598 A | 12/1988 | Ziegast |
| 4,839,343 A | 6/1989 | Waeber et al. |
| 4,868,274 A | 9/1989 | Gupta et al. |
| 4,904,479 A | 2/1990 | Illum |
| 4,906,474 A | 3/1990 | Langer et al. |
| 4,996,335 A | 2/1991 | Bodor |
| 4,999,417 A | 3/1991 | Domb |
| 5,145,684 A | 9/1992 | Liversidge et al. |
| 5,540,930 A | 7/1996 | Guy et al. |
| 5,543,158 A | 8/1996 | Gref et al. |
| 5,552,160 A | 9/1996 | Liversidge et al. |
| 5,578,325 A | 11/1996 | Domb et al. |
| 5,612,053 A * | 3/1997 | Baichwal et al. ............ 424/440 |
| 5,665,331 A | 9/1997 | Bagchi et al. |
| 5,718,921 A | 2/1998 | Mathiowitz et al. |
| 5,747,061 A | 5/1998 | Amselem et al. |
| 5,916,596 A | 6/1999 | Desai et al. |
| 5,985,309 A | 11/1999 | Edwards et al. |
| 6,197,346 B1 | 3/2001 | Mathiowitz et al. |
| 6,270,806 B1 | 8/2001 | Liversidge et al. |
| 7,060,299 B2 * | 6/2006 | Alavattam et al. ............ 424/491 |
| 7,153,524 B2 | 12/2006 | Yoshihara et al. |
| 7,157,426 B2 * | 1/2007 | Quay et al. ...................... 514/12 |
| 7,163,697 B2 | 1/2007 | Hanes et al. |
| 7,534,449 B2 | 5/2009 | Saltzman et al. |
| 7,763,278 B2 | 7/2010 | Cooper et al. |
| 7,795,237 B2 | 9/2010 | Ahmed et al. |
| 2002/0035264 A1 | 3/2002 | Kararli et al. |
| 2002/0068090 A1 | 6/2002 | Bell et al. |
| 2003/0086895 A1 | 5/2003 | Hanes et al. |
| 2004/0175429 A1 | 9/2004 | Alavattam et al. |
| 2004/0209807 A1 | 10/2004 | Quay et al. |
| 2004/0258763 A1 | 12/2004 | Bell |
| 2005/0101676 A1 | 5/2005 | Fahl et al. |
| 2006/0083781 A1 | 4/2006 | Shastri et al. |
| 2006/0210622 A1 | 9/2006 | Pace et al. |
| 2007/0292524 A1 | 12/2007 | Ringe et al. |

(Continued)

FOREIGN PATENT DOCUMENTS

| AU | 2006220411 A1 | 10/2006 |
| CA | 2564982 A1 | 11/2005 |

(Continued)

OTHER PUBLICATIONS

Newman et al (J Biomed Mater Res, 60: 480-486, 2002).*
Singh et al (PNAS, 97(2): 811-816, 2000).*
Norris et al (J Appl Poly Sci, 63: 1481-1492, 1997).*
Dawson et al (Vet Rec, 127(13):338, 1990).*
Dawson et al., "Transport of Polymeric Nanoparticle Gene Carriers in Gastric Mucus," Biotechnol. Prog. 20:851-857 (2004).
Vila et al., "Transport of PLA-PEG Particles Across the Nasal Mucosa: Effect of Particle Size and PEG Coating Density," Journal of Controlled Release 98:231-244 (2004).
Delgado et al., "Radiolabelled Biodegradable Microspheres for Lung Imaging," European Journal of Pharmaceutics and Biopharmaceutics 50:227-236 (2000).
De Campos et al., "The Effect of a PEG Versus a Chitosan Coating on the Interaction of Drug Colloidal Carriers with the Ocular Mucosa," European Journal of Pharmaceutical Sciences 20:73-81 (2003).
Norris et al., "Effect of Size, Surface Charge, and Hydrophobicity on the Translocation of Polystyrene Microspheres Through Gastrointestinal Mucin," Journal of Applied Polymer Science 63(11):1481-1492 (1997).

(Continued)

*Primary Examiner* — Marcia S Noble
*Assistant Examiner* — Magdalene Sgagias
(74) *Attorney, Agent, or Firm* — Foley Hoag LLP

(57) ABSTRACT

The invention generally relates to polymeric particles suitable for transporting bioactive agents across mucosal barriers. The invention also relates to methods of making and using those polymeric particles.

28 Claims, 15 Drawing Sheets

(56) References Cited

U.S. PATENT DOCUMENTS

| | | |
|---|---|---|
| 2008/0102128 A1 | 5/2008 | Constancis et al. |
| 2008/0166414 A1 | 7/2008 | Hanes et al. |
| 2008/0248125 A1 | 10/2008 | Irache Garreta et al. |
| 2009/0074786 A1 | 3/2009 | Dor et al. |
| 2009/0087494 A1 | 4/2009 | Kompella et al. |
| 2009/0155182 A1 | 6/2009 | Mauro et al. |
| 2009/0226531 A1 | 9/2009 | Lyons et al. |
| 2010/0074957 A1 | 3/2010 | Robinson et al. |
| 2010/0215580 A1 | 8/2010 | Hanes et al. |
| 2012/0121718 A1 | 5/2012 | Lai et al. |

FOREIGN PATENT DOCUMENTS

| | | |
|---|---|---|
| EP | 0 692 510 | 12/2004 |
| JP | 2007-534729 | 11/2007 |
| WO | WO-95/03356 | 2/1995 |
| WO | WO-95/22318 | 8/1995 |
| WO | WO-98/29097 | 7/1998 |
| WO | WO-99/01498 | 1/1999 |
| WO | WO-0046147 A2 | 8/2000 |
| WO | WO-0238127 A2 | 5/2002 |
| WO | WO-02/053189 | 7/2002 |
| WO | WO-2005/072710 | 8/2005 |
| WO | WO-2005/104648 | 11/2005 |
| WO | WO-2006044660 A2 | 4/2006 |
| WO | WO-2007/133808 | 11/2007 |
| WO | WO-2008030557 A2 | 3/2008 |
| WO | WO-2008033924 A2 | 3/2008 |
| WO | WO-2011097347 A2 | 8/2011 |
| WO | WO-2011106702 A2 | 9/2011 |

OTHER PUBLICATIONS

Denis-Mize et al., "Plasmid DNA Adsorbed onto Cationic Microparticles Mediates Target Gene Expression and Antigen Presentation by Dendritic Cells," Gene Therapy 7:2105-2112 (2000).

Norris et al., "The Uptake and Translocation of Microparticles through GI Mucin," Pharmaceutical Research 12(9):S233 (1995).

U.S. Appl. No. 12/310,751, filed Mar. 6, 2009, Hanes et al.

Albertsson et al., Characterization and Degradation fo Aliphatic Polyanhydrides. British Polyner J. 23, 205-12 (1990).

Brorson et al., Mutational Analysis of Avidity and Fine Specificity of Anti-Levan Antibodies. J. Immunol. Vole. 163, pp. 6694-6701 (1999).

Brummell et al., Probing the combining site of an anti-carbohydrate antibody by saturation-mutagenesis: role of the heavy-chain CDR3 residues. Biochemistry vol. 32 pp. 1180-1187 (1993).

Burks et al., In vitro scanning saturation mutagenesis of an antibody binding pocket. PNAS vol. 94. pp. 412-417 (1997).

Chan, et al. Phase behavior and miscibility in blends of poly(sebacic anhydride)/ poly(ethylene glycol). Biomaterials 23, 2353-58 (2002).

Colman, Effects of amino acid sequence changes on antibody-antigen interactions. Research in Immunol. vol. 145 pp. 33-36 (1994).

Dawson et al., Enhanced Viscoelasticity of Human Cystic Fibrotic Sputum Correlates with Increasing Microheterogeneity in Particle Transport. The Journal of Biological Chemistry. vol. 278 pp. 50393-50401 (2003).

Dufner et al., Harnessing phage and ribosome display for antibody optimisation. Trends Biotechnol. vol. 24, No. 11, pp. 523-529 (2006).

Ehrhardt et al., Drug Absorption by the Respiratory Mucosa: Cell Culture Models and Participate Drug Carriers. Journal of Aerosol Medicine. vol. 15, No. 2. pp. 131-139 (2002).

Jang et al., The structural basis for DNA binding by an anti-DNA autoantibody. Molec. Immunol. vol. 35, pp. 1207-1217 (1998).

Jiang et al. Preparation, characterization and degradation characteristics of polyanhydrides containing poly(ethylene gylcol). Polym Int. 48, 47-52 (1999).

Jiang et al., Pulsatile protein release from a laminated device comprising of polyanhydrides and pH-sensitive complexes. Int. J. Pharmaceutics 194, 51-60 (2000).

Kobayashi et al., Tryptophan H33 plays an important role in pyrimidine (6-4) pyrimidone photoproduct binding by a high-affinity antibody. Protein Engineering vol. 12, pp. 879-884 (1999).

Lai et al., Rapid transport of large polymeric nanoparticles in fresh undiluted human mucus. PNAS vol. 104, No. 5 pp. 1482-1487 (2007).

Lipman et al., Monoclonal Versus Polyclonal Antibodies: Distinguishing Characteristics, Applications, and Information Resources. ILAR Journal vol. 46, No. 3. pp. 258-268 (2005).

Liyan, Q. et al. Compatibility and degradation of new polyphosphazene/polyanhydride blend. Gaofenzi Xuebao 5, 660-664 (2001), Chemical Abstracts Service, Accession No. 2001:817417.

Peracchia, M. T. et al. PRG-coated nanospheres from amphiphilic diblock and multiblock copolymers: Investigation of their drug encapsulation and release characteristics. J. Controlled Release 46, 223-231 (1997).

Qiu, L. Y. & Zhu, K. J. Design of a core-shelled polymer cylinder for potential programmable drug delivery. Int. J. Pharm. 219, 151-160 (2001).

Rolland et al., Direct Fabrication and Harvesting of Monodisperse, Shape-Specific Nanobiomaterials. J. Am. Chem. Soc. vol. 127 pp. 10096-10100 (2005).

Shuai, X. et al. Synthesis and characterization of several degradable aliphatic polyanhydrides. J. Beijing Inst. Tech. 5, 130-136 (1996), Chemical Abstract Service, Accession No. 1997:364424.

Wu, C. et al. Novel Nanoparticles Formed via Self-Assembly of Poly(ethylene glycol-*b*-sebacic anhydride) and Their Degradation in Water. Macromolecules 33, 9040-9043 (2000).

Giannavola et al., "Influence of Preparation Conditions on Acyclovir-Loaded Poly-*d,l*-Lactic Acid Nanospheres and Effect of PEG Coating on Ocular Drug Bioavailability," Pharmaceutical Research, 20(4):584-590 (2003).

International Search Report for PCT/US2005/002556 mailed Jun. 19, 2006.

Cone, A. (1999) in Mucosal Immunology, eds Ogra PL, Mestecky J, Lamm ME, Strober W, Bienenstock J, McGhee JR (Academic, San Diego), 2nd Ed, pp. 43-64.

Bures et al., "Surface modifications and molecular imprinting of polymers in medical and pharmaceutical applications," Journal of Controlled Release, 72:25-33 (2001).

Choy et al., "Mucoadhesive Microparticles Engineered for Ophthalmic Drug Delivery," J Phys Chem Solids, Author manuscript; available in PMC 2010, Jul. 23, pp. 1-8. (Published in final edited form as: J Phys Chem Solids. May 2008 ; 69(5-6): 1533-1536. doi:10.1016/j.jpcs.2007.10.043.).

Huang et al., "Molecular aspects of muco- and bioadhesion: Tethered structures and site-specific surfaces," Journal of Controlled Release, 65:63-71 (2000).

Peppas et al., "Poly(ethylene glycol)-containing hydrogels in drug delivery," Journal of Controlled Release, 62:81-87 (1999).

Serra et al., "Design of poly(ethylene glycol)-tethered copolymers as novel mucoadhesive drug delivery systems," European Journal of Pharmaceutics and Biopharmaceutics, 63:11-18 (2006).

Serra et al., "Engineering Design and Molecular Dynamics of Mucoadhesive Drug Delivery Systems as Targeting Agents," Eur J Pharm Biopharm., Author manuscript; available in PMC 2010, Mar. 1, pp. 1-24. (Published in final edited form as: Eur J Pharm Biopharm. Mar. 2009 ; 71(3): 519-528. doi:10.1016/j.ejpb.2008.09.022.).

Wang et al., "Addressing the PEG Mucoadhesivity Paradox to Engineer Nanoparticles that 'Slip' through the Human Mucus Barrier," Angew. Chem. Int. Ed., 47:1-5 (2008).

Yoncheva et al., "Evaluation of bioadhesive potential and intestinal transport of pegylated poly(anhydride) nanoparticles," International Journal of Pharmaceutics, 334:156-165 (2007).

Apgar et al., "Multiple-Particle Tracking Measurements of Heterogeneities in Solutions of Actin Filaments and Actin Bundles," Biophysical Journal, 79:1095-1106 (2000).

Batrakova et al., "Pluronic Block Copolymers: Evolution of Drug Delivery Concept from Inert Nanocarriers to Biological Response Modifiers," NIH Public Access Author Manuscript pp. 1-25; Published in final edited form as: J. Control Release, 130(2):98-106 (2008).

Bhalla, Kapil N., "Microtubule-targeted anticancer agents and apoptosis," Oncogene, 22:9075-9086 (2003).

(56) References Cited

OTHER PUBLICATIONS

Boskey et al., "A Self-Sampling Method to Obtain Large Volumes of Undiluted Cervicovaginal Secretions," Sexually Transmitted Diseases, 30(2):107-109 (2003).
Cone, Richard A., "Barrier properties of mucus," Advanced Drug Delivery Reviews, 61:75-85 (2009).
Cu et al., "Controlled surface modification with poly(ethylene)glycol enhances diffusion of PLGA nanoparticles in human cervical mucus," NIH Public Access Author Manuscript, pp. 1-18; Published in final edited form as: Mol Pharm., 6(1):173-181 (2009).
Donaldson et al., "A placebo-controlled multi-centred evaluation of an anaesthetic gel (Oraqix®) for periodontal therapy," J Clin Periodontol, 30:171-175 (2003).
Dumortier et al., "A Review of Poloxamer 407 Pharmaceutical and Pharmacological Characateristics," Pharmaceutical Research, 23(12):2709-2728 (2006).
Emanuele, R. Martin, "FLOCOR™: a new anti-adhesive rheologic agent," Exp. Opin. Invest. Drugs, 7(7):1193-1200 (1998).
Escobar-Chávez et al., "Applications of Thermo-Reversible Pluronic F-127 Gels in Pharmaceutical Formulations," J Pharm Pharmaceut Sci, 9(3):339-358 (2006).
Farokhzad et al., "Targeted nanoparticle-aptamer bioconjugates for cancer chemotherapy in vivo," PNAS, 103(16):6315-6320 (2006).
Fu, J. et al., "New polymeric carriers for controlled drug delivery following inhalation or injection," Biomaterials, 23:4425-4433 (2002).
Kim et al., "Comparison of the pharmacokinetic profiles of two locally administered doxycycline gels in crevicular fluid and saliva," Journal of Clinical Periodontology, 31:286-292 (2004).
Knowles et al., "Mucus clearance as a primary innate defense mechanism for mammalian airways," The Journal of Clinical Investigation, 109(5):571-577 (2002).
Lai et al., "Altering Mucus Rheology to 'Solidfy' Human Mucus at the Nanoscale," PLoS ONE, 4(1):1-6, e4294 (2009).
Lai et al., "Mucus-penetrating nanoparticles for drug and gene delivery to mucosal tissues," NIH Public Access Author Manuscript, pp. 1-36; Published in final edited form as: Adv Drug Deliv Rev. 61(2):158-171 (2009).
Lo et al., "Formulation design and pharmaceutical development of a novel controlled release form of azithromycin for single-dose therapy," Drug Development and Industrial Pharmacy, 35(12):1522-1529 (2009).
Mu et al., "Vitamin E TPGS used as emulsifier in the solvent evaporation/extraction technique for fabrication of polymeric nanospheres for controlled release of paclitaxel (Taxol®)," Journal of Controlled Release, 80:129-144 (2002).
Peppas et al., "Ultrapure poly(vinyl alcohol) hydrogels with mucoadhesive drug delivery characteristics," European Journal of Pharmaceutics and Biopharmaceutics, 43:51-58 (1997).
Pillai et al., "Polymers in drug delivery," Current Opinion in Chemical Biology, (5):447-451 (2001).
Prego et al., "The potential of chitosan for the oral administration of peptides," Expert Opin Drug Deliv, 2(5):843-854 (2005).
Pui, Ching-Hon, "Rasburicase: a potent uricolytic agent," Expert Opin. Pharmacother, 3(4):433-442 (2002).
Rodeheaver et al., "Pluronic F-68*: A Promising New Skin Wound Cleanser," Ann Emerg Med, 9(11):572/51-576/55 (1980).
Shakesheff et al., "The Adsorption of Poly(vinyl alcohol) to Biodegradable Microparticles Studied by X-Ray Photoelectron Spectroscopy (XPS)," Journal of Colloid and Interface Science, 185:538-547 (1997).
Singla et al., "Paclitaxel and its formulations," International Journal of Pharmaceutics, 235:179-192 (2002).
Suh et al., "Real-time multiple-particle tracking: applications to drug and gene delivery," Advanced Drug Delivery Reviews, 57:63-78 (2005).
Tang et al., "Biodegradable polymer nanoparticles that rapidly penetrate the human mucus barrier," PNAS, 106(46):19268-19273 (2009).
Yoo et al., "Biodegradable Nanoparticles Containing Doxorubicin-PLGA Conjugate for Sustained Release," Pharmaceutical Research, 16(7):1114-1118 (1999).
Fresta et al., "Ocular Tolerability and In Vivo Bioavailability of Poly(ethylene glycol) (PEG)-Coated Polyethyl-2-Cyanoacrylate Nanosphere-Encapsulated Acyclovir," J. Pharm. Sci., 90(3):288-297 (2001).
Giunchedi et al., "Emulsion Spray-Drying for the Preparation of Albumin-Loaded PLGA Microspheres," Drug Dev. Ind. Pharm., 27(7):745-750 (2001).
Yoncheva et al., "Bioadhesive properties of pegylated nanoparticles," Expert Opin. Drug Deliv., 2(2):205-218 (2005).
International Preliminary Report on Patentability and Written Opinion for PCT/US2005/002556 mailed Jul. 31, 2006.
International Preliminary Report on Patentability and Written Opinion for PCT/US2007/019522 mailed Mar. 10, 2009.
International Search Report for PCT/US2007/019522 mailed Mar. 12, 2008.
International Search Report for PCT/US2011/059321 mailed Feb. 8, 2012.
Office Action for JP Application No. 2009-527422, mailed Nov. 27, 2012.
Perry, R.H., "Sorbent materials and sorption-process analysis," Perry's Chemical Engineers' Handbook, 6th ed., McGraw-Hill, 1984, pp. 16-5, 16-6.
Declaration of Dr. Alexey Popov in the Opposition against EP Patent 2061433, Jun. 5, 2013.
Prasad et al., "Confocal microscopy of colloids," Journal of Physics Condensed Matter, 19, 113102,1-25 (2007).
Webster's Ninth New Collegiate Dictionary, 1983, p. 58.

\* cited by examiner

A

B

C

C. PLGA-DDAB/DNA

Time 0
30 min.

Figure 9

| Particles | D(μm²/s) |
|---|---|
| 200 nm PS | $5 \times 10^{-5}$ |
| PLGA-DDAB/DNA | $2 \times 10^{-3}$ |
| PEI | no motion |
| PEI-PEG | $5 \times 10^{-4}$ |
| PEG-SA | $2 \times 10^{-2}$ |

DRUGS AND GENE CARRIER PARTICLES THAT RAPIDLY MOVE THROUGH MUCOUS BARRIERS

RELATED APPLICATIONS

This application is a national stage filing under 35 U.S.C. 371 of International Application PCT/US2005/002556, filed Jan. 28, 2005, which claims priority from United States Provisional Application Nos. 60/539,773, filed Jan. 28, 2004 and 60/579,533, filed Jun. 14, 2004, the specifications of all of which are incorporated by reference herein. International Application PCT/US2005/002556 was published under PCT Article 21(2) in English.

STATEMENT OF GOVERNMENTAL INTEREST

This invention was made with government support under grant number CTS0210718, awarded by the National Science Foundation. The government has certain rights in the invention.

BACKGROUND

The primary component of mucus is higher molecular weight mucin glycoproteins, which form numerous covalent and noncovalent bonds with other mucin molecules and various constituents, including DNA, alginate, and hyaluronan. Hanes et al., Gene therapy in the lung. in Pharmaceutical Inhalation Aerosol Technology, 2d ed.; Marcel Dekker Inc.: New York, 2003; pp. 489-539. Reconstituted mucus formulated from pig gastric, human cervical, and tracheobronchial mucins display similar mucus structures, with large rod or fiberlike aggregates of 5 nm in diameter and 100-5000 nm in length. Khanvilkar et al., Adv. Drug Deliv. Rev. 2001 48, 173-193. The condensed and complex microstructure of the mucus network gives rise to a highly viscoelastic gel, which significantly impedes the transport rates of large macromolecules and nanoparticles. Saltzman et al., Biophys. J. 1994, 66, 508-515; Sanders et al., Am. J. Respir. Crit. Care Med. 2002, 162, 1905-1911; Olmsted et al., Biophys. J. 2001 81, 1930-1937. Immobilized nanoparticles are subject to bacterial and enzymatic degradation and may also be cleared from the body by normal mucus clearance mechanisms. Although clearance rates are anatomically determined, mucus turnover rates in the GI tract are estimated as between 24 and 48 h. Khanvilkar et al., supra. In the lungs, clearance rates are dependent on the region of particle deposition; however, normal tracheal mucus velocities, albeit more rapid than mucus velocities in the peripheral lung, range from 1-10 mm/min and turnover times are less than 1 h. Cone, R. A. Mucus. In Mucosal Immunology, 2nd ed.; Academic Press: San Diego, Calif., 1999; pp. 43064. As a result, it is desirable to have drug and gene carriers, which are capable of efficiently traversing mucus layers coating mucosal surfaces.

SUMMARY OF THE INVENTION

Accordingly, the present invention provides bioactive agent carriers and methods of making and using them. In particular, the carriers include polymeric or liposomal particles that are capable of efficiently traversing mucus layers coating mucosal surfaces. The polymeric particles generally comprise a pharmaceutically acceptable polymer core and a surface-altering agent. The liposomal particles generally comprise a liposome core and a surface-altering agent. The polymeric or liposomal particles may comprise one or more bioactive agents and/or imaging agents. The polymeric or liposomal particles may also comprise a targeting moiety.

In one aspect, a polymeric particle comprises a pharmaceutically acceptable polymer core and a surface-altering agent that is embedded or enmeshed in the particle's surface or that is disposed (e.g., by coating, adsorption, covalent linkage, or other process) on the surface of the particle. The surface-altering agent may be a bioactive agent itself. For example, in certain embodiment, a polymeric particle may comprise a pharmaceutically acceptable polymer and a nucleic acid coating the surface of the particle. In such embodiments, the nucleic acid molecule may alter the surface of the particle and make it mucus resistant. In certain other embodiments, a polymeric particle comprises a pharmaceutically acceptable polymer and a protein (e.g., serum albumin) disposed on the surface of the particle. The protein may alter the surface of the particle and make it mucus resistant. In any of these embodiments, the polymeric particle may comprise an imaging agent, e.g., that may include a diagnostic agent and/or a detectable label. For example, the nucleic acid or the protein included in the polymeric particle may comprise an imaging agent itself, e.g., a detectable label can be attached to the DNA or the protein. Alternatively, the polymeric particle may comprise an imaging agent that is separate from the nucleic acid or the protein, e.g., encapsulated in the core or disposed on or coupled to the surface. Additionally, the polymeric particle may comprise a targeting moiety or molecule coupled to the polymeric particle and/or the protein or nucleic acid, and the targeting moiety can help deliver the nucleic acid, the protein, and/or the imaging or diagnostic agent to a targeted location in a patient.

In certain embodiments, a polymeric particle comprises a pharmaceutically acceptable polymer core, a bioactive agent (e.g., a drug or medicament) encapsulated in the core, and a surface-altering agent that is embedded or enmeshed in the particle's surface, or disposed (e.g., by coating, adsorption, covalent linkage, or other process) on the surface of the particle and that alters the surface of the particle, e.g., to make it mucus resistant. The polymeric particle may comprise an imaging agent, e.g., a diagnostic agent and/or a detectable label. The encapsulated bioactive agent may be or comprise an imaging agent itself, e.g., a detectable label may be attached to a therapeutic agent. Alternatively, the polymeric particle may comprise an imaging agent that is separate from the bioactive agent. Additionally, the polymeric particle may comprise a targeting moiety or molecule coupled to the polymeric particle, and the targeting moiety can help deliver the bioactive agent and/or the imaging agent to a desirable location in a patient.

Alternatively, a polymeric particle may comprise a pharmaceutically acceptable polymer core, a surface-altering agent, e.g., a surfactant, that is embedded or enmeshed in the particle's surface, or disposed (e.g., by coating, adsorption, covalent linkage, or other process) on the surface of the particle and that alters the surface of the particle, such as by making it mucus-resistant, and a bioactive agent disposed on the polymeric particle. The bioactive agent may be coated or otherwise disposed on the surface of the polymeric particle, or be coupled to the polymeric particle by, e.g., covalent linkage, complexation, or other process. In certain such embodiments, the surface-altering agent is selected to promote adhesion or complexation of the bioactive agent to the surface of the particle. In such embodiments, the surface-altering agent and/or the bioactive agent may contribute to mucus-resistant properties of the modified particles. The polymeric particles may comprise an imaging agent, such as a diagnostic agent and/or a detectable label. The bioactive agent coated or disposed on the surface of the particle or coupled to the particle may be or comprise an imaging agent itself, e.g., a detectable label can be attached to a therapeutic agent. Alternatively, the polymeric particle may comprise an imaging agent that is separate from the bioactive agent, e.g., encapsulated in the core or disposed on or coupled to its surface. Additionally, the polymeric particle may comprise a targeting moiety or molecule coupled to the polymeric particle, and the targeting moiety can help deliver the bioactive agent and/or the imaging agent to a targeted location in a patient.

The present invention also provides a polymeric particle, comprising a polymeric particle having regions of polyethylene glycol or its derivatives that are presented on the surface of the particle. The polymeric particle may optionally comprise an additional surface-altering agent. The polymeric particle may further comprise a bioactive agent and/or a targeting moiety.

Bioactive agents according to the invention include but are not limited to a DNA (e.g., a gene therapy vector or plasmid), an RNA (e.g., an RNAi construct or molecule), a small molecule, a peptidomimetic, a protein or peptide, and a combination thereof.

The surface-altering agent may increase charge or hydrophilicity of the polymeric or liposomal particle, or otherwise decrease interactions between the particle and mucus, thereby promoting motility through mucus. The surface-altering agent may enhance the average rate at which the polymeric or liposomal particles, or a fraction of the particles, move in or through mucus. Examples of suitable surface-altering agents include but are not limited to anionic protein (e.g., serum albumin), nucleic acids, surfactants such as cationic surfactants (e.g., dimethyldioctadecyl-ammonium bromide), sugars or sugar derivatives (e.g., cyclodextrin), polyethylene glycol, mucolytic agents, or other non-mucoadhesive agents. Certain agents, e.g., cyclodextrin, may form inclusion complexes with other molecules and can be used to form attachments to additional moieties and facilitate the functionalization of the particle surface and/or the attached molecules or moieties.

The polymeric particles of the invention have many applications. In particular, they are well-suited for making pharmaceutical compositions, particularly those for which the route of administration involves the particles passing through a mucosal barrier. For example, the polymeric particles are particularly suitable for making pharmaceutical compositions to be formulated as nasal spray, such that the pharmaceutical compositions can be delivered across a nasal mucus layer. Similarly, the polymeric particles are particularly suitable for making pharmaceutical compositions for delivery via gastrointestinal, respiratory, rectal, and/or vaginal tissues.

A pharmaceutically acceptable polymer may be a poly(D, L-lactic-co-glycolic) acid, polyethylenimine, dioleyltrimethyammoniumpropane/dioleyl-sn-glycerolphosphoethianolamine, polysebacic anhydride, or other polymer formed from clinically acceptable or approved monomers. Examples of clinically approved monomers include but are not limited to monomers of sebacic acid and 3-bis(carboxyphenoxy)propane. Other polymers or copolymers described herein can also be employed to make the polymeric particles of the invention.

In certain embodiments, a bioactive agent is a therapeutic agent or an imaging agent (e.g., a diagnostic agent). Examples of therapeutic agents include but are not limited to a DNA, an RNA, a small molecule, a peptidomimetic, a protein, and a combination thereof. In certain embodiments, the imaging agent further comprises a detectable label.

In certain embodiments, a polymeric particle of the invention may further comprise a targeting agent or molecule. A polymeric particle may also further or alternatively comprise an adjuvant.

In certain embodiments, a polymeric particle of the invention may further comprise an agent covalently linked to the polymeric particle. The agent may be a bioactive agent, such as for example a drug. The agent may preferably be a hydrophilic agent, such that through its covalent linkage to the polymeric particle, the agent alters charge or hydrophilicity of the particle, e.g., to increase the particle's mucus resistance. The covalent linkage may be cleavable under biological conditions.

Certain embodiments provides polymeric particles that are, on average, less than 100 μm, 10 μm, 1 μm, 500 nm, and more preferably 200 nm in diameter or nanoparticles.

Further, the present invention provides polymeric particles that can pass through a mucosal barrier at a greater rate than certain other polymeric particles, e.g., unmodified polystyrene particles. A polymeric particle of the invention may pass through a mucosal barrier at a rate that is at least 2, 5, 10, 20, 30, 50, 100, 200, 500, 1000- or greater fold higher than, e.g., an unmodified polystyrene particle of a similar size.

A second aspect of the invention relates to a pharmaceutical composition comprising a polymeric particle of the invention.

Also provided is an inhaler comprising a polymeric particle of the invention.

A third aspect relates to a use of a polymeric particle of the invention in the manufacture of a medicament for the treatment, prevention, or diagnosis of a condition in a patient.

A fourth aspect relates to a method for transfecting a cell comprising contacting the cell with a polymeric particle of the invention that comprises a nucleic acid. A polymeric particle of the invention comprising a nucleic acid may transfect a cell at a higher efficiency, e.g., at 2, 5, 10, 20, 50, 100 or greater-fold higher efficiency, than the naked nucleic acid, e.g., in the presence of a mucosal barrier.

A fifth aspect related to a method for treating, preventing, or diagnosing a condition in a patient, comprising administering to the patient a pharmaceutical composition of the invention. In certain embodiments, the polymeric particle in a pharmaceutical composition of the invention transports through a mucosal barrier in the patient.

A sixth aspect relates to a method for preparing polymeric particles of the invention. Any method suitable for preparing polymeric particles, in particular, nanoparticles, may be employed. An exemplary method may include: combining a pharmaceutically acceptable polymer with a surface-altering agent to form a mixture in an organic solvent; adding a bioactive agent to the mixture; removing the solvent from the mixture; and obtaining a polymeric particle suspension. The method may further include passing the polymeric particle suspension through a filter. The method may also include removing impurities from the polymeric particle suspension. The method may also comprise a centrifugation step to pellet the polymeric particles. Another exemplary method may include: obtaining microparticles or preferably nanoparticles using a pharmaceutically acceptable polymer and coupling (e.g., by coating, covalent linkage, or co-localization) to the surface of the microparticles or nanoparticles a surface-altering agent, e.g., a polyethylene glycol, a nucleic acid, or a protein. A method of the invention may further include: coupling (e.g., by coating, covalent linkage, or co-localization) to the polymeric particles an imaging agent, a detectable label, or a targeting moiety.

BRIEF DESCRIPTION OF THE DRAWINGS

FIG. 9 is a table showing the effective diffusion coefficients of nanoparticles in synthetic mucus, as calculated from 4-D confocal microscopy (see FIG. 8).

DETAILED DESCRIPTION OF THE INVENTION

1. Overview

Figure 1:
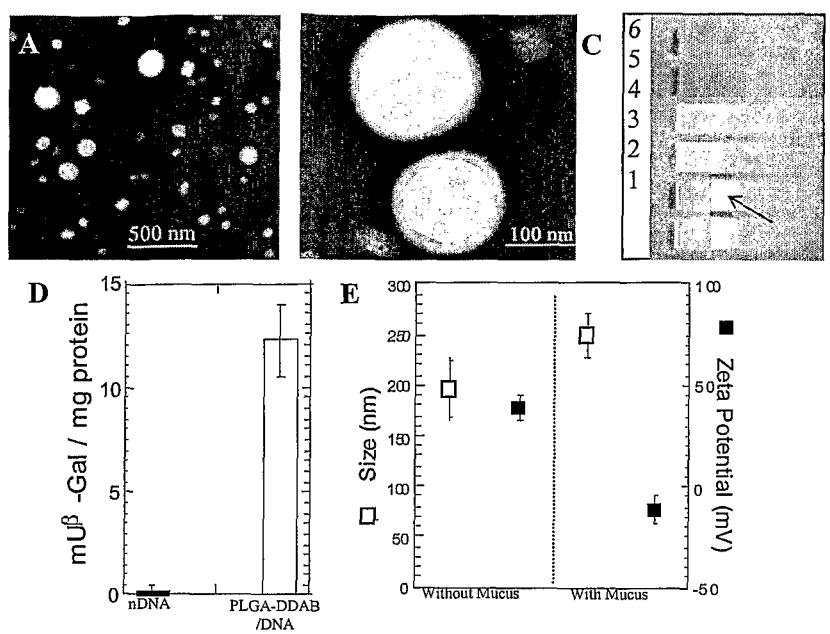
FIG. 1 illustrates the characterization of PLGA-DDAB/DNA nanoparticles. (A,B) Transmission electron micrographs showed nanoparticle sizes <300 nm. (C) Complexation of salmon testes DNA with cationic PLGA-DDAB nanoparticles was assayed by UV gel electrophoresis. Lanes 1 and 2: free DNA (arrow shows primary band ~2 kb). Lanes 3 and 4: PLGA-DNA (no DDAB). Lanes 5 and 6: PLGA-DDAB/DNA nanoparticles. (D) PLGA-DDAB/DNA nanoparticles transfect Cos-7 cells with 50-fold increase in transfection efficiency compared to naked DNA. (E) The size and ζ-potential of PLGA-DDAB/DNA nanoparticles were assayed in 150 mM NaCl and in PGM. Size values represent the average value from 10 measurements, while the ζ-potential values were an average of three measurements (n=2 separate batches).

Cationic microparticles with DNA adsorbed to their surfaces have been shown to efficiently transfect cells in vitro. E.g., Singh et al., Proc Natl Acad Sci USA 2000, 97, 811-816; Singh et al., Pharm Res 2001, 18, 1476-1479; Denis-Mize et al., Gene Ther 2000, 7, 2105-2112. However, obtaining high transfection efficiencies in vivo is often limited by particle transport through extracellular barriers, including the mucosal barrier, which has been described as the foremost barrier to transfection in mucus-covered cells. See, e.g., Ferrari et al., Gene Ther 2001, 8, 1380-1386; Yonemitsu et al., Nat Biotechnol 2000, 18, 970-973.

High MW poly(ethylene glycol) (PEG) has been used as a mucoadhesive added to polymeric systems for its reported ability to interpenetrate into the mucus network (Bures et al., J. Controlled Release, (2001) 72:25-33; Huang et al., J. Controlled Release, (2000) 65:63-71; Peppas et al., J. Controlled Release, (1999) 62:81-87) and hydrogen bond to mucins Willits et al., Biomaterials, (2001) 22:445-452; Sanders et al., J. Controlled Release, (2003) 87:117-129). However, as shown in the examples below, modifying the surface of different particle types formulated from polymers and liposomes with PEG decreased the adsorption of mucus components to the particle surface and allowed more rapid transport through mucus with a reduced number of adhesive particles.

Modification of particle surface with other polymers, proteins, surfactants, sugars, nucleic acids, or non-mucoadhesive materials may also result in increased transport in mucus and other adhesive biological fluids, such as serum. For example, as shown below, modification of particle surface by the adsorption of hydrophilic DNA to the surface of hydrophobic PLGA-DDAB nanoparticles increases transport in mucus. Additionally, non-specific adsorption of polylysine (PLL) or bovine serum albumin (BSA) to hydrophobic polystyrene particles increases transport in mucus. These findings also indicate that the attachment of PEG to the surface of particles formulated from a variety of materials greatly reduces the effects of mucin adsorption, increases transport rates, and provides increased particle stability. Other molecules such as surfactants or polymers, including poly (aspartic acid), and proteins, such as heparin, may also increase transport rates in mucus.

Accordingly, the present invention relates to polymeric or liposomal particles and compositions comprising them, such as pharmaceutical compositions for the delivery of biologically active and/or therapeutic agents, e.g., for the prevention or treatment of a disease or other condition in a patient, particularly, for delivery across mucosal barriers in the patient. The present invention also provides a polymeric particle comprising a polymer having regions of polyethylene glycol that are presented on the surface of the particle. In certain embodiments, biodegradable and biocompatible polymers may be used to transport or carry an adsorbed or encapsulated therapeutic agent across a mucosal barrier present in any mucosal surface, e.g., gastrointestinal, nasal, respiratory, rectal, or vaginal mucosal tissues in a patient. Agents that may be adsorbed or encapsulated in the subject compositions include imaging and diagnostic agents (such as radiopaque agents, labeled antibodies, labeled nucleic acid probes, dyes, such as colored or fluorescent dyes, etc.) and adjuvants (radiosensitizers, transfection-enhancing agents, chemotactic agents and chemoattractants, peptides that modulate cell adhesion and/or cell mobility, cell permeabilizing agents, vaccine potentiators, inhibitors of multidrug resistance and/or efflux pumps, etc.). The present invention also relates to methods of making and/or administering such compositions, e.g., as part of a treatment regimen, for example, by inhalation, or by injection, e.g., subcutaneously, intramuscularly, or intravenously.

2. Definitions

For convenience, before further description of the present invention, certain terms employed in the specification, examples, and appended claims are collected here. These definitions should be read in light of the remainder of the disclosure and understood as by a person of skill in the art.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the head and neck area, or any other medical device suitable for entering or remaining positioned within the preselected anatomic area.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 μL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

Exemplary biocompatible and biodegradable polymers disclosed in U.S. Patent Application Publication No. 20030086895 may be employed to make the polymeric particles of the present invention.

The term "biodegradable" is art-recognized, and includes polymers, compositions and formulations, such as those described herein, that are intended to degrade during use. Biodegradable polymers typically differ from non-biodegradable polymers in that the former may degrade during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both general types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible."

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day or less (e.g., 4-8 hours) on exposure to a physiological solution with a pH between 6 and 8 having a temperature of between 25 and 37° C. In other embodiments, the polymer degrades in a period of between about one hour and several weeks, depending on the desired application.

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area. The term further includes those devices that transport or accomplish the instillation of the compositions of the present invention towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "microspheres" is art-recognized, and includes substantially spherical colloidal structures, e.g., formed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized. In certain embodiments, the nanospheres, nanocapsules and nanoparticles have a size an average diameter of about 500, 200, 100, 50 or 10 nm.

A composition comprising microparticles or nanoparticles may include particles of a range of particle sizes. In certain embodiments, the particle size distribution may be uniform, e.g., within less than about a 20% standard deviation of the median volume diameter, and in other embodiments, still more uniform, e.g., within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrasternal injection and infusion.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

Viscosity is understood herein as it is recognized in the art to be the internal friction of a fluid or the resistance to flow exhibited by a fluid material when subjected to deformation. The degree of viscosity of the polymer can be adjusted by the molecular weight of the polymer, as well as by varying the proportion of its various monomer subunits; other methods for altering the physical characteristics of a specific polymer will be evident to practitioners of ordinary skill with no more than routine experimentation. The molecular weight of the polymer used in the composition of the invention can vary widely, depending on whether a rigid solid state (higher molecular weights) is desirable, or whether a fluid state (lower molecular weights) is desired.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, J. Pharm. Sci. 66: 1-19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that, when incorporated into a polymer of the present invention, produces some desired effect at a reasonable benefit/risk ratio applicable to any medical treatment. In certain embodiments, the term refers to that amount necessary or sufficient to eliminate or reduce sensations of pain for a period of time. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The term "$ED_{50}$" is art-recognized. In certain embodiments, $ED_{50}$ means the dose of a drug that produces 50% of its maximum response or effect, or, alternatively, the dose that produces a pre-determined response in 50% of test subjects or preparations.

The term "$LD_{50}$" is art-recognized. In certain embodiments, $LD_{50}$ means the dose of a drug that is lethal in 50% of test subjects. The term "therapeutic index" is an art-recognized term that refers to the therapeutic index of a drug, defined as $LD_{50}/ED_{50}$.

The terms "incorporated" and "encapsulated" are art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "biocompatible plasticizer" is art-recognized, and includes materials which are soluble or dispersible in the compositions of the present invention, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyltrihexyl citrate (c. 20 weight percent or less), butyl benzyl phthalate, dibutylphthalate, dioctylphthalate, n-butyryl tri-n-hexyl citrate, diethylene glycol dibenzoate (c. 20 weight percent or less) and the like.

3. Polymeric Particles and Related Compositions

The present invention provides polymeric particles, such as microparticles or nanoparticles. In certain embodiments, a polymeric particle comprises a pharmaceutically acceptable polymer, a bioactive agent, and a surface-altering agent that makes the surface of the polymeric particle mucus resistant.

In alternative embodiments, a polymeric particle comprises a pharmaceutically acceptable polymer and a surface-altering agent that is also a bioactive agent. In certain such embodiments, the particle further comprises an adhesion-promoting agent, such as dimethyldioctadecyl-ammonium bromide or other cation-bearing additives, that promotes adhesion of the surface-altering agent to the surface of the particle. The surface-altering agent may increase particle transport rates in mucus.

Examples of the surface-altering agents include but are not limited to anionic protein (e.g., bovine serum albumin), surfactants (e.g., cationic surfactants such as for example dimethyldioctadecyl-ammonium bromide), sugars or sugar derivatives (e.g., cyclodextrin), nucleic acids, and polyethylene glycol. Surface-altering agents may also include mucolytic agents, e.g., rhDase or N-acetylcysteine. A mucolytic agent can be administered separately or concomitantly with a polymeric particle, or as a surface-altering agent of the polymeric particle (e.g., coated upon, covalently coupled to, co-localized with, or encapsulated within the particle) of the invention to improve transport across a mucosal barrier. Certain agents, e.g., cyclodextrin, may form inclusion complexes with other molecules and can be used to form attachments to additional moieties and facilitate the functionalization of the particle surface and/or the attached molecules or moieties.

Examples of surfactants include but are not limited to L-α-phosphatidylcholine (PC), 1,2-dipalmitoylphosphatidycholine (DPPC), oleic acid, sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil, lecithin, oleic acid, and sorbitan trioleate.

A pharmaceutically acceptable polymer may be a poly (lactic-co-glycolic) acid (PLGA), poly(D,L-lactic-co-glycolic) acid), polyethylenimine, dioleyltrimethyammoniumpropane/dioleyl-sn-glycerolphosphoethanolamine, polysebacic anhydrides, or other polymers formed from clinically approved monomers. Examples of clinically approved monomers include but are not limited to monomers of sebacic acid and 1,3-bis(carboxyphenoxy)propane.

A pharmaceutically acceptable polymer may be a polyanhydride polymer comprising repeated subunits of Formula A and Formula B, and, optionally, subunits of Formula C, as depicted below: below:

Formula A:

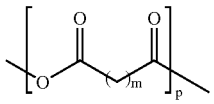

Formula B:

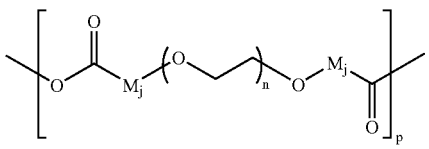

Formula C:

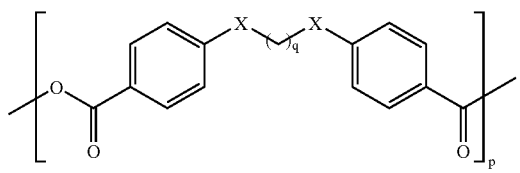

wherein, as valence and stability permit,

M represents, independently for each occurrence, a substituted or unsubstituted methylene, e.g., $CH_2$, CH(Me), $CF_2$, CH(OH), C=O, etc., preferably $CH_2$ or, for an occurrence of M adjacent to O, C=O;

X is absent or, independently for each occurrence, represents a heteroatom selected from NR, O, and S, preferably O;

R represents, independently for each occurrence, H or lower alkyl;

j represents, independently for each occurrence, an integer from 0 to 16, preferably from 1 to 9;

m represents, independently for each occurrence, an integer from 4 to 20, preferably from 8 to 14, even more preferably 10;

n represents, independently for each Occurrence, an integer from 4 to 500, preferably from 10 to 200;

p represents, independently for each occurrence, an integer from 1 to 60, preferably from 4 to 40; and q represents, independently for each occurrence, an integer from 1 to 20, preferably from 2 to 10, even more preferably from 2 to 6.

In certain embodiments, m, n, and q each, independently, represent a constant value throughout the polymer, i.e., m, n, and q do not vary within a subunit of Formula A, B, or C, or within different subunits of the same formula, within a sample of polymer or a polymer chain.

In certain embodiments, the polymer may contain monomeric units other than those subunits represented by Formulae A, B, and C. In preferred embodiments, however, the polymer consists essentially of subunits of Formulae A, B, and C.

In certain embodiments, a polymer of the present invention has the formula —[K]$_n$—, wherein each occurrence of K represents a subunit of Formula A or B or, optionally, C, as set forth above. Polymer strands may be capped (terminated) with hydroxyl groups (to form carboxylic acids), acyl groups (to form anhydrides), alkoxy groups (to form esters), or any other suitable capping groups.

In certain embodiments, the subunits of Formula B have a molecular weight between 200 and 1000 daltons, while in other embodiments, the subunits of Formula B have a molecular weight between 4000 and 10,000 daltons. In some embodiments, the subunits of Formula B have molecular weights which vary throughout the polymer between 200 daltons and 10,000 or more daltons, while in other embodiments, the subunits of Formula B have molecular weights that vary only within a narrow range (e.g., 200-300 daltons, or 2,000-3,000 daltons).

In certain embodiments, subunits of Formula B make up between 1 and 80% of the polymer, by weight, preferably between 5 and 60%. In certain embodiments, subunits of Formula C, if present, may make up between 1% and 80% of the polymer, by weight, preferably between 5 and 60%. In certain embodiments, subunits of Formula A make up between 10% and 99% of the polymer, by weight, preferably between 15% and 95%.

Each subunit may repeat any number of times, and one subunit may occur with substantially the same frequency, more often, or less often than another subunit, such that both subunits may be present in approximately the same amount, or in differing amounts, which may differ slightly or be highly disparate, e.g., one subunit is present nearly to the exclusion of the other.

In certain instances, the polymers are random copolymers, in which the different subunits and/or other monomeric units are distributed randomly throughout the polymer chain. In part, the term "random" is intended to refer to the situation in which the particular distribution or incorporation of monomeric units in a polymer that has more than one type of monomeric unit is not directed or controlled directly by the synthetic protocol, but instead results from features inherent to the polymer system, such as the reactivity, amounts of subunits and other characteristics of the synthetic reaction or other methods of manufacture, processing or treatment.

In certain embodiments, the polymeric chains of the subject compositions, e.g., which include repetitive elements shown in any of the subject formulas, have molecular weights ($M_w$) ranging from about 2000 or less to about 300,000, 600,000 or 1,000,000 or more daltons, or alternatively at least about 10,000, 20,000, 30,000, 40,000, or 50,000 daltons, more particularly at least about 100,000 daltons. Number-average molecular weight ($M_n$) may also vary widely, but generally falls in the range of about 1,000 to about 200,000 daltons, preferably from about 10,000 to about 100,000 daltons and, even more preferably, from about 8,000 to about 50,000 daltons. Most preferably, $M_n$ varies between about 12,000 and 45,000 daltons. Within a given sample of a subject polymer, a wide range of molecular weights may be present. For example, molecules within the sample may have molecular weights that differ by a factor of 2, 5, 10, 20, 50, 100, or more, or that differ from the average molecular weight by a factor of 2, 5, 10, 20, 50, 100, or more.

One method to determine molecular weight is by gel permeation chromatography ("GPC"), e.g., mixed bed columns, $CH_2Cl_2$ solvent, light scattering detector, and off-line dn/dc. Other methods are known in the art.

Other polymers that may be employed to make the polymeric particles of the invention include but are not limited to cyclodextrin-containing polymers, in particular cationic cyclodextrin-containing polymers, such as those described in U.S. Pat. No. 6,509,323, poly(caprolactone) (PCL), ethylene vinyl acetate polymer (EVA), poly(lactic acid) (PLA), poly (L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, poly(propylene fumarate), polyoxymethylene, poloxamers, poly(ortho)esters, poly(butyric acid), poly(valeric acid), poly(lactide-co-caprolactone), trimethylene carbonate, polyvinylpyrrolidone, and the polymers described in Shieh et al., 1994, J. Biomed. Mater. Res., 28, 1465-1475, and in U.S. Pat. No. 4,757,128, Hubbell et al., U.S. Pat. Nos. 5,654,381; 5,627,233; 5,628,863; 5,567,440; and 5,567,435. Other suitable polymers include polyorthoesters (e.g. as disclosed in Heller et al., 2000, Eur. J. Pharm. Biopharm., 50:121-128), polyphosphazenes (e.g. as disclosed in Vandorpe et al., 1997, Biomaterials, 18:1147-1152), and polyphosphoesters (e.g. as disclosed in Encyclopedia of Controlled Drug Delivery, pp. 45-60, Ed. E. Mathiowitz, John Wiley & Sons, Inc. New York, 1999), as well as blends and/or block copolymers of two or more such polymers. The carboxyl termini of lactide- and glycolide-containing polymers may optionally be capped, e.g. by esterification, and the hydroxyl termini may optionally be capped, e.g. by etherification or esterification.

Copolymers of two or more polymers described above, including block and/or random copolymers, may also be employed to make the polymeric particles of the invention.

The invention also contemplates employing copolymers of PEG or derivatives thereof (such as units of Formula B, above) with any of the polymers described above to make the polymeric particles of the invention. In certain embodiments, the PEG or derivatives may locate in the interior positions of the copolymer. Alternatively, the PEG or derivatives may locate near or at the terminal positions of the copolymer. In certain embodiments, the microparticles or nanoparticles are formed under conditions that allow regions of PEG to phase separate or otherwise locate to the surface of the particles. While in certain embodiments, the surface-localized PEG regions alone may perform the function of a surface-altering agent, in other embodiments these copolymeric particles comprise an additional surface-altering agent.

In certain embodiments, the subject polymers are soluble in one or more common organic solvents for ease of fabrication and processing. Common organic solvents include such solvents as 2,2,2-trifluoroethanol, chloroform, dichloromethane, dichloroethane, 2-butanone, butyl acetate, ethyl butyrate, acetone, ethyl acetate, dimethylacetamide, N-methyl pyrrolidone, dimethylformamide, and dimethylsulfoxide.

In certain embodiments, the subject polymeric particles and compositions include a bioactive agent. A bioactive agent may be a therapeutic agent, a diagnostic agent, or an imaging agent. Examples of therapeutic agents include but are not limited to a DNA, an RNA, a small molecule, a peptidomimetic, a protein, or a combination thereof. In certain embodiments, the diagnostic or imaging agent further comprises a detectable label.

A bioactive agent may be a nucleic acid, e.g., a DNA useful in gene therapy. Alternatively or additionally, an RNA may be employed as a bioactive agent. The RNA may be an RNAi molecule or construct. RNAi refers to "RNA interference," by which expression of a gene or gene product is decreased by introducing into a target cell one or more double-stranded RNAs which are homologous to the gene of interest (particularly to the messenger RNA of the gene of interest). RNAi may also be achieved by introduction of a DNA:RNA complex wherein the antisense strand (relative to the target) is RNA. Either strand may include one or more modifications to the base or sugar-phosphate backbone. Any nucleic acid preparation designed to achieve an RNA interference effect is referred to herein as an siRNA construct.

Alternatively, an antisense nucleic acid is employed as a bioactive agent. An antisense nucleic acid may bind to its target by conventional base pair complementarity, or, for example, in the case of binding to DNA duplexes, through specific interactions in the major groove of the double helix. The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556, Lemaitre et al., 1987, Proc. Natl. Acad. Sci. 84:648-652, PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

"Small molecule" as used herein is meant to refer to a molecule having a molecular weight of less than about 3 kD and most preferably less than about 1.5 kD. Extensive libraries of chemical and/or biological mixtures comprising arrays of small molecules and/or fungal, bacterial, or algal extracts can be screened with any of the assays known in the art to obtain a desirable bioactive agent for use in or with a polymeric particle of the invention.

Peptidomimetics are compounds in which at least a portion of a peptide, such as a therapeutic peptide, is modified, and the three-dimensional structure of the peptidomimetic remains substantially the same as that of the peptide. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry.

The term "protein," "polypeptide," and "peptide" are used interchangeably herein and generally refer to a polymer formed by at least two amino acids linked via a peptide bond.

Imaging agents (e.g., detectable labels or bioactive agents linked to a detectable label), therapeutic agents, and targeting moieties, such as those described in U.S. Patent Application Publication No. 20030049203, are also contemplated and can be employed with the polymeric particles of the present invention.

In certain embodiments, a polymeric particle of the invention comprises an imaging agent that may be further attached to a detectable label (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A polymeric particle including such a moiety may be used as an imaging agent and be administered in an amount effective for diagnostic use in a mammal such as a human. In this manner, the localization and accumulation of the imaging agent can be detected. The localization and accumulation of the imaging agent may be detected by radioscintiography, nuclear magnetic resonance imaging, computed tomography, or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The means of detection used to detect the label is dependent of the nature of the label used and the nature of the biological sample used, and may also include fluorescence polarization, high performance liquid chromatography, antibody capture, gel electrophoresis, differential precipitation, organic extraction, size exclusion chromatography, fluorescence microscopy, or fluorescence activated cell sorting (FACS) assay.

In certain embodiments, a bioactive agent or targeting moiety may be covalently coupled to a polymeric particle of the invention. In such embodiments, the bioactive agent may preferably be a hydrophilic or charged agent, such that its presence on the surface of the particle increases charge or hydrophilicity of the particle or otherwise increases the particle's mucus resistance. The covalent linkage may be selected to be cleaved under biological conditions, e.g., by chemical or enzymatic hydrolysis or other cleavage processes.

In certain embodiments, a polymeric particle of the invention may further comprise a targeting moiety or molecule. The targeting molecule may be covalently linked to any other component of the polymeric particle, such as the polymer or a surface-altering agent. The targeting molecule may also be co-localized with a polymeric particle, using methods known in the art. The targeting molecule may direct the particle, and thus the included bioactive agent, to a desirable target or location in a patient.

Covalent linkage may be effected by various methods known in the art. Moieties, such as surface-altering agents, adhesion-promoting agents, bioactive agents, targeting agents, and other functional moieties discussed herein, to be covalently linked to the surface of a particle (pendant moieties) may be coupled to the surface after formation of the particle, or may be coupled to one or more components prior to formation of the particle, such that, by chance or molecular self-assembly, the moieties locate to the surface of the particle during particle formation, and thus become embedded or enmeshed in the surface of the particle. Moieties may be coupled to the surface of a formed particle in any order or by any attachment that maintains the desired activity of each component, whether in its linked state or following cleavage of a biocleavable linkage, for example. Pendant moieties may be affixed to particles or components by linking functional groups present at the termini of those moieties or components or by linking appropriate functional groups present at any location on either component. Alternatively, the various components may be linked indirectly through a tether molecule as is well known in the art.

Numerous chemical cross-linking methods are known and potentially applicable for conjugating the various portions of the instant constructs. Many known chemical cross-linking methods are non-specific, i.e., they do not direct the point of coupling to any particular site on the molecule. As a result, use of non-specific cross-linking agents may attack functional sites or sterically block active sites, rendering the conjugated molecules inactive.

For coupling simple molecules, it is often possible to control the location of coupling by using protecting groups, functional group-selective reactions, or the differential steric accessibility of particular sites on the molecules. Such strategies are well known to those skilled in the art of chemical synthesis. Protecting groups may include but are not limited to N-terminal protecting groups known in the art of peptide syntheses, including t-butoxy carbonyl (BOC), benzoyl (Bz), fluoren-9-ylmethoxycarbonyl (Fmoc), triphenylmethyl(trityl) and trichloroethoxycarbonxyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

A preferred approach to increasing coupling specificity of complex molecules is direct chemical coupling to a functional group found only once or a few times in one or both of the molecules to be cross-linked. For example, in many proteins, cysteine, which is the only protein amino acid containing a thiol group, occurs only a few times. Also, for example, if a peptide contains no lysine residues, a cross-linking reagent specific for primary amines will be selective for the amino terminus of that peptide. Successful utilization of this approach to increase coupling specificity requires that the molecule have the suitable reactive residues in areas of the molecule that may be altered without loss of the molecule's biological activity.

Coupling of the two constituents can be accomplished via a coupling or conjugating agent. There are several intermolecular cross-linking reagents which can be utilized. See, e.g., Means, G. E. and Feeney, R. E., Chemical Modification of Proteins, Holden-Day, 1974, pp. 39-43. Among these reagents are, for example, J-succinimidyl 3-(2-pyridyldithio) propionate (SPDP) or N,N'-(1,3-phenylene)bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m, m'-dinitrodiphenylsulfone (which forms irreversible cross-linkages with amino and phenolic groups); dimethyl adipimidate (which is specific for amino groups); phenol-1, 4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of peptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Heterobifunctional cross-linkers provide the ability to design more specific coupling methods for conjugating two chemical entities, thereby reducing the occurrences of unwanted side reactions such as homo-protein polymers. A wide variety of heterobifunctional cross-linkers are known in the art. Examples of heterobifunctional cross-linking agents are succinimidyl 4-(N-maleimidomethyl)-cyclohexane-1-carboxylate (SMCC), N-succinimidyl (4-iodoacetyl)aminobenzoate (SIAB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), succinimidyl 6-[3-(2-pyridyldithio)propionate]hexanoate (LC-SPDP)succinimidyl 4-(N-maleimidomethyl)-cyclohexane-1-carboxylate (SMCC), m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Another reactive group useful as part of a heterobifunctional cross-linker is a thiol reactive group. Common thiol-reactive groups include maleimides, halogens, and pyridyl disulfides. Maleimides react specifically with free sulfhydryls (cysteine residues) in minutes, under slightly acidic to neutral (pH 6.5-7.5) conditions. Haloalkyl groups (e.g., iodoacetyl functions) react with thiol groups at physiological pH's. Both of these reactive groups result in the formation of stable thioether bonds.

In addition to the heterobifunctional cross-linkers, there exist a number of other cross-linking agents including homobifunctional and photoreactive cross-linkers. Disuccinimidyl-suberate (DSS), bismaleimidohexane (BMH) and dimethylpimelimidate-2HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a review of protein coupling techniques, see Means et al. (1990) Bioconjugate Chemistry 1:2-12, incorporated by reference herein.

Many cross-linking reagents yield a conjugate that is essentially non-cleavable under cellular conditions. However, some cross-linking reagents contain a covalent bond, such as a disulfide, that is cleavable under cellular conditions. For example, dithiobis(succinimidylpropionate) (DSP), Traut's reagent and N-succinimidyl 3-(2-pyridyldithio)propionate (SPDP) are well-known cleavable cross-linkers. The use of a cleavable cross-linking reagent may permit the moiety, such as a therapeutic agent, to separate from the construct after delivery to the target. Direct disulfide linkages may also be useful. Additional cleavable linkages are known in the art and may be employed to advantage in certain embodiments of the present invention.

Many methods for linking compounds, such as proteins, labels, and other chemical entities, to nucleotides are known in the art. Some new cross-linking reagents such as n-maleimidobutyryloxy-succinimide ester (GMBS) and sulfo-GMBS, have reduced immunogenicity. Substituents have been attached to the 5' end of preconstructed oligonucleotides using amidite or H-phosphonate chemistry, as described by Ogilvie, K. K., et al., Pure and Appl Chem (1987) 59:325, and by Froehler, B. C., Nucleic Acids Res (1986) 14:5399. Substituents have also been attached to the 3' end of oligomers, as described by Asseline, U., et al., Tet Lett (1989) 30:2521. This last method utilizes 2,2'-dithioethanol attached to a solid support to displace diisopropylamine from a 3' phosphonate bearing the acridine moiety and is subsequently deleted after oxidation of the phosphorus. Other substituents have been bound to the 3' end of oligomers by alternate methods, including polylysine (Bayard, B., et al., Biochemistry (1986) 25:3730; Lemaitre, M., et al., Nucleosides and Nucleotides (1987) 6:311) and, in addition, disulfides have been used to attach various groups to the 3' terminus, as described by Zuckerman, R., et al., Nucleic Acids Res (1987) 15:5305. It is known that oligonucleotides which are substituted at the 3' end show increased stability and increased resistance to degradation by exonucleases (Lancelot, G., et al., Biochemistry (1985) 24:2521; Asseline, U., et al., Proc Natl Acad Sci USA (1984) 81:3297). Additional methods of attaching non-nucleotide entities to oligonucleotides are discussed in U.S. Pat. Nos. 5,321,131 and 5,414,077.

Alternatively, an oligonucleotide may include one or more modified nucleotides having a group attached via a linker arm to the base. For example, Langer et al (Proc. Natl. Acad. Sci. U.S.A., 78(11):6633-6637, 1981) describes the attachment of biotin to the C-5 position of dUTP by an allylamine linker arm. The attachment of biotin and other groups to the 5-position of pyrimidines via a linker arm is also discussed in U.S. Pat. No. 4,711,955. Nucleotides labeled via a linker arm attached to the 5- or other positions of pyrimidines are also suggested in U.S. Pat. No. 4,948,882. Bisulfite-catalyzed transamination of the N.sup.4-position of cytosine with bifunctional amines is described by Schulman et al. (Nucleic Acids Research, 9(5): 1203-1217, 1981) and Draper et al (Biochemistry, 19: 1774-1781, 1980). By this method, chemical entities are attached via linker arms to cytidine or cytidine-containing polynucleotides. The attachment of biotin to the N4-position of cytidine is disclosed in U.S. Pat.

No. 4,828,979, and the linking of moieties to cytidine at the $N^4$-position is also set forth in U.S. Pat. Nos. 5,013,831 and 5,241,060. U.S. Pat. No. 5,407,801 describes the preparation of an oligonucleotide triplex wherein a linker arm is conjugated to deoxycytidine via bisulfite-catalyzed transamination. The linker arms include an aminoalkyl or carboxyalkyl linker arm. U.S. Pat. No. 5,405,950 describes cytidine analogs in which a linker arm is attached to the N4-position of the cytosine base.

Numerous cross-linking reagents, including the ones discussed above, are commercially available. Detailed instructions for their use are readily available from the commercial suppliers. A general reference on protein cross-linking and conjugate preparation is: S. S. Wong, Chemistry of Protein Conjugation and Cross-Linking, CRC Press (1991).

Chemical cross-linking may include the use of spacer arms, i.e., linkers or tethers. Spacer arms provide intramolecular flexibility or adjust intramolecular distances between conjugated moieties and thereby may help preserve biological activity. A spacer arm may be in the form of a peptide moiety comprising spacer amino acids. Alternatively, a spacer arm may be part of the cross-linking reagent, such as in "long-chain SPDP" (Pierce Chem. Co., Rockford, Ill., cat. No. 21651H).

A variety of coupling or crosslinking agents such as protein A, carbodiimide, dimaleimide, dithio-bis-nitrobenzoic acid (DTNB), N-succinimidyl-5-acetyl-thioacetate (SATA), and N-succinimidyl-3-(2-pyridyldithio)propionate (SPDP), 6-hydrazinonicotimide (HYNIC), $N_3S$ and $N_2S_2$ can be used in well-known procedures to synthesize targeted constructs. For example, biotin can be conjugated to an oligonucleotide via DTPA using the bicyclic anhydride method of Hnatowich et al. Int. J. Appl. Radiat. Isotop. 33:327 (1982).

In addition, sulfosuccinimidyl 6-(biotinamido)hexanoate (NHS-LC-biotin, which can be purchased from Pierce Chemical Co. Rockford, Ill.), "biocytin," a lysine conjugate of biotin, can be useful for making biotin compounds due to the availability of a primary amine. In addition, corresponding biotin acid chloride or acid precursors can be coupled with an amino derivative of the therapeutic agent by known methods. By coupling a biotin moiety to the surface of a particle, another moiety may be coupled to avidin and then coupled to the particle by the strong avidin-biotin affinity, or vice versa.

In certain embodiments where a polymeric particle comprises PEG moieties on the surface of the particle, the free hydroxyl group of PEG may be used for linkage or attachment (e.g., covalent attachment) of additional molecules or moieties to the particle.

Imaging labels may be coupled to a polymeric particle by covalent bonding directly or indirectly to an atom of the polymer or surface-altering agent, or the label may be non-covalently or covalently associated with the particle through a chelating structure or through an auxiliary molecule such as mannitol, gluconate, glucoheptonate, tartrate, and the like.

Any suitable chelating structure may be used to provide spatial proximity between a radionuclide and the particle through covalent or noncovalent association. Many such chelating structures are known in the art. Preferably, the chelating structure is an $N_2S_2$ structure, an $N_3S$ structure, an $N_4$ structure, an isonitrile-containing structure, a hydrazine containing structure, a HYNIC (hydrazinonicotinic acid)-containing structure, a 2-methylthionicotinic acid-containing structure, a carboxylate-containing structure, or the like. In some cases, chelation can be achieved without including a separate chelating structure, because the radionuclide chelates directly to atom(s) in or pendant from the particle, for example to oxygen atoms in the polymer or a polyethylene glycol surface-altering agent.

Radionuclides may be placed in spatial proximity to a particle using known procedures which effect or optimize chelation, association, or attachment of the specific radionuclide to a component of the particle or a moiety pendant from the particle's surface. For example, when $^{123}I$ is the radionuclide, the imaging agent may be labeled in accordance with the known radioiodination procedures such as direct radioiodination with chloramine T, radioiodination exchange for a halogen or an organometallic group, and the like. When the radionuclide is $^{99}mTc$, the imaging agent may be labeled using any method suitable for attaching $^{99}mTc$ to a ligand molecule. Preferably, when the radionuclide is $^{99}mTc$, an auxiliary molecule such as mannitol, gluconate, glucoheptonate, or tartrate is included in the labeling reaction mixture, with or without a chelating structure. More preferably, $^{99}mTc$ is placed in spatial proximity to the targeting molecule by reducing $^{99}mTcO_4$ with tin in the presence of mannitol and the targeting molecule. Other reducing agents, including tin tartrate or non-tin reductants such as sodium dithionite, may also be used to make an imaging agent according to the invention.

In general, labeling methodologies vary with the choice of radionuclide, the moiety to be labeled and the clinical condition under investigation. Labeling methods using $^{99}mTc$ and $^{111}In$ are described for example in Peters, A. M. et al., Lancet 2: 946-949 (1986); Srivastava, S. C. et al., Semin. Nucl. Med. 14(2):68-82 (1984); Sinn, H. et al., Nucl. Med. (Stuttgart) 13:180, 1984); McAfee, J. G. et al., J. Nucl. Med. 17:480-487, 1976; McAfee, J. G. et al., J. Nucl. Med. 17:480-487, 1976; Welch, M. J. et al., J. Nucl. Med. 18:558-562, 1977; McAfee, J. G., et al., Semin. Nucl. Med. 14(2):83, 1984; Thakur, M. L., et al., Semin. Nucl. Med. 14(2):107, 1984; Danpure, H. J. et al., Br. J. Radiol., 54:597-601, 1981; Danpure, H. J. et al., Br. J. Radiol. 55:247-249, 1982; Peters, A. M. et al., J. Nucl. Med. 24:39-44, 1982; Gunter, K. P. et al., Radiology 149:563-566, 1983; and Thakur, M. L. et al., J. Nucl. Med. 26:518-523, 1985.

Polymeric particles can be characterized using standard methods of high field NMR spectra as well as IR, MS, and optical rotation. Elemental analysis, TLC, and/or HPLC can be used as a measure of purity. A purity of at least about 80%, preferably at least about 90%; more preferably at least about 95% and even more preferably at least about 98% is preferred. TLC and/or HPLC can also be used to characterize such compounds.

Once prepared, candidate polymeric particles can be screened for ability to carry their bioactive agent(s) across a mucosal barrier. The candidate particles may also be tested for ability to transfect a cell, if the carried bioactive agent is a nucleic acid. In addition, stability of a polymeric particle can be tested by incubating the compound in serum, e.g., human serum, and measuring the potential degradation of the compound over time. Stability can also be determined by administering the compound to a subject (human or non-human), obtaining blood samples at various time periods (e.g., 30 min, 1 hour, 24 hours) and analyzing the blood samples for derived or related metabolites.

A "drug," "therapeutic agent," or "medicament," is a biologically, physiologically, or pharmacologically active substance that acts locally or systemically in the human or animal body. A subject composition may include any active substance.

Various forms of the medicaments or drug may be used which are capable of being carried by the polymeric particles across mucosal barriers into adjacent tissues or fluids. They may be acidic, basic, or salts. They may be neutral molecules, polar molecules, or molecular complexes capable of hydrogen bonding. They may be in the form of ethers, esters, amides and the like, including prodrugs which are biologically activated when injected into the human or animal body, e.g., by cleavage of an ester or amide. An analgesic agent is also an example of a "medicament." Any additional medicament in a subject composition may vary widely with the purpose for the composition. The term "medicament" includes without limitation, vitamins; mineral supplements; substances used for the treatment, prevention, diagnosis, cure or mitigation of disease or illness; substances which affect the structure or function of the body; or pro-drugs, which become biologically active or more active after they have been placed in a predetermined physiological environment.

Plasticizers and stabilizing agents known in the art may be incorporated in polymeric particles of the present invention. In certain embodiments, additives such as plasticizers and stabilizing agents are selected for their biocompatibility. In certain embodiments, the additives are lung surfactants, such as 1,2-dipalmitoylphosphatidycholine (DPPC) and L-α-phosphatidylcholine (PC).

In other embodiments, spheronization enhancers facilitate the production of subject polymeric particles that are generally spherical in shape. Substances such as zein, microcrystalline cellulose or microcrystalline cellulose co-processed with sodium carboxymethyl cellulose may confer plasticity to the subject compositions as well as impart strength and integrity. In particular embodiments, during spheronization, extrudates that are rigid, but not plastic, result in the formation of dumbbell shaped particles and/or a high proportion of fines, and extrudates that are plastic, but not rigid, tend to agglomerate and form excessively large particles. In such embodiments, a balance between rigidity and plasticity is desirable. The percent of spheronization enhancer in a formulation typically range from 10 to 90% (w/w).

In certain embodiments, a subject composition includes an excipient. A particular excipient may be selected based on its melting point, solubility in a selected solvent (e.g., a solvent that dissolves the polymer and/or the therapeutic agent), and the resulting characteristics of the particles.

Excipients may comprise a few percent, about 5%, 10%, 15%, 20%, 25%, 30%, 40%, 50%, or higher percentage of the subject compositions.

Buffers, acids and bases may be incorporated in the subject compositions to adjust their pH. Agents to increase the diffusion distance of agents released from the polymer matrix may also be included.

4. Applications: Therapeutic and Diagnostic Compositions

In part, a polymer particle of the present invention includes a biocompatible and preferably biodegradable polymer, such as any polymer discussed above, optionally including any other biocompatible and optionally biodegradable polymer mentioned above or known in the art. The invention provides pharmaceutical compositions that include one or more polymeric particles. A pharmaceutical composition may be a therapeutic composition and/or a diagnostic or imaging composition.

A. Physical Structures of the Subject Compositions

The subject polymeric particles, e.g., microparticles or preferably nanoparticles, comprise polymeric matrices. Microparticles typically comprise a biodegradable polymer matrix and a bioactive agent, e.g., the bioactive agent is encapsulated by or adsorbed to the polymer matrix. Microparticles can be formed by a wide variety of techniques known to those of skill in the art. Examples of microparticle-forming techniques include, but are not limited to, (a) phase separation by emulsification and subsequent organic solvent evaporation (including complex emulsion methods such as oil-in-water emulsions, water-in-oil emulsions, and water-oil-water emulsions); (b) coacervation-phase separation; (c) melt dispersion; (d) interfacial deposition; (e) in situ polymerization; (f) spray-drying and spray-congealing; (g) air suspension coating; and (h) pan and spray coating. These methods, as well as properties and characteristics of microparticles are disclosed in, for example, U.S. Pat. Nos. 4,652,441; 5,100,669; 4,526,938; WO 93/24150; EPA 0258780 A2; U.S. Pat. Nos. 4,438,253; and 5,330,768, the entire disclosures of which are incorporated by reference herein.

To prepare particles of the present invention, several methods can be employed depending upon the desired application of the delivery vehicles. Suitable methods include, but are not limited to, spray-drying, freeze-drying, air drying, vacuum drying, fluidized-bed drying, milling, co-precipitation and critical fluid extraction. In the case of spray-drying, freeze-drying, air drying, vacuum drying, fluidized-bed drying and critical fluid extraction; the components (stabilizing polyol, bioactive material, buffers, etc.) are first dissolved or suspended in aqueous conditions. In the case of co-precipitation, the components are mixed in organic conditions and processed as described below. Spray-drying can be used to load the particle with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning or transmission electron microscopy. Spherically shaped nanoparticles are used in certain embodiments, e.g., for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such, an endocytosis process will likely depend on the size of any particle.

B. Dosages and Formulations of the Subject Compositions

In most embodiments, the subject polymers will incorporate the substance to be delivered in an amount sufficient to deliver to a patient a therapeutically effective amount of an incorporated therapeutic agent or other material as part of a diagnostic, prophylactic, or therapeutic treatment. The desired concentration of active compound in the particle will depend on absorption, inactivation, and excretion rates of the drug as well as the delivery rate of the compound from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Further, the amounts of bioactive substances will vary depending upon the relative potency of the agents selected. Additionally, the optimal concentration and/or quantities or amounts of any particular therapeutic agent may be adjusted to accommodate variations in the treatment parameters. Such treatment parameters include the polymer composition of a particular preparation, the identity of the therapeutic agent utilized, and the clinical use to which the preparation is put, e.g., the site treated, the type of patient, e.g., human or non-human, adult or child, and the nature of the disease or condition.

The concentration and/or amount of any therapeutic agent or other adsorbed or encapsulated material for a given subject composition may readily identified by routine screening in animals, e.g., rats, by screening a range of concentration and/or amounts of the material in question using appropriate assays. Known methods are also available to assay local tissue concentrations, diffusion rates from particles and local blood flow before and after administration of therapeutic formulations according to the invention. One such method is microdialysis, as reviewed by T. E. Robinson et al., 1991, MICRODIALYSIS IN THE NEUROSCIENCES, Techniques, volume 7, Chapter 1. The methods reviewed by Robinson may be applied, in brief, as follows. A microdialysis loop is placed in situ in a test animal. Dialysis fluid is pumped through the loop. When particles according to the invention are injected adjacent to the loop, released drugs are collected in the dialysate in proportion to their local tissue concentrations. The progress of diffusion of the active agents may be determined thereby with suitable calibration procedures using known concentrations of active agents.

In certain embodiments, the dosage of the subject invention may be determined by reference to the plasma concentrations of the therapeutic agent or other encapsulated materials. For example, the maximum plasma concentration ($C_{max}$) and the area under the plasma concentration-time curve from time 0 to infinity may be used.

The polymeric compositions of the present invention may be administered by various means, depending on their intended use, as is well known in the art. For example, if subject compositions are to be administered orally, it may be formulated as tablets, capsules, granules, powders or syrups. Alternatively, formulations of the present invention may be administered parenterally as injections (intravenous, intramuscular, or subcutaneous), drop infusion preparations, or suppositories. For application by the ophthalmic mucous membrane route, subject compositions may be formulated as eyedrops or eye ointments. These formulations may be prepared by conventional means, and, if desired, the subject compositions may be mixed with any conventional additive, such as a binder, a disintegrating agent, a lubricant, a corrigent, a solubilizing agent, a suspension aid, an emulsifying agent or a coating agent.

In addition, in certain embodiments, subject compositions of the present invention maybe lyophilized or subjected to another appropriate drying technique such as spray drying.

The subject compositions may be administered once, or may be divided into a number of smaller doses to be administered at varying intervals of time, depending in part on the release rate of the compositions and the desired dosage.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

Particles, particularly nanoparticles, which may be administered in inhalant or aerosol formulations according to the invention comprise one or more agents, such as adjuvants, diagnostic agents, imaging agents, or therapeutic agents useful in inhalation therapy.

The particle size of the particulate medicament should be such as to permit inhalation of substantially all of the medicament into the lungs upon administration of the aerosol formulation and will thus desirably be less than 20 microns, preferably in the range 1 to 10 microns, e.g., 1 to 5 microns. The particle size of the medicament may be reduced by conventional means, for example by milling or micronisation.

The final aerosol formulation desirably contains 0.005-90% w/w, preferably 0.005-50%, more preferably 0.005-5% w/w, especially 0.01-1.0% w/w, of medicament relative to the total weight of the formulation.

It is desirable, but by no means required, that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. As used herein "substantially free" means less than 1% w/w based upon the propellant system, in particular less than 0.5%, for example 0.1% or less.

The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol and propylene glycol, preferably ethanol. In general, only small quantities of polar adjuvants (e.g., 0.05-3.0% w/w) may be required to improve the stability of the dispersion—the use of quantities in excess of 5% w/w may tend to dissolve the medicament. Formulations in accordance with the invention may preferably contain less than 1% w/w, e.g., about 0.1% w/w, of polar adjuvant. However, the formulations of the invention are preferably substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated C1-C6 hydrocarbon.

Optionally, the aerosol formulations according to the invention may further comprise one or more surfactants. The surfactants must be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Preferred surfactants are lecithin, oleic acid, and sorbitan trioleate.

The formulations of the invention may be prepared by dispersal of the particles in the selected propellant and/or co-propellant in an appropriate container, e.g., with the aid of sonication. Preferably, the particles are suspended in co-propellant and filled into a suitable container. The valve of the container is then sealed into place and the propellant introduced by pressure filling through the valve in the conventional manner. The particles may be thus suspended or dissolved in a liquified propellant, sealed in a container with a metering valve and fitted into an actuator. Such metered dose inhalers are well known in the art. The metering valve may meter 10 to 500 µL and preferably 25 to 150 µL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers. The carriers and stabilizers vary with the requirements of the particular composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Ophthalmic formulations, eye ointments, powders, solutions and the like, are also contemplated as being within the scope of this invention.

Certain pharmaceutical compositions of this invention suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Microparticle and/or nanoparticle compositions may be suspended in a pharmaceutically acceptable solution, such as saline, Ringer's solution, dextran solution, dextrose solution, sorbitol solution, a solution containing polyvinyl alcohol (from about 1% to about 3%, preferably about 2%), or an osmotically balanced solution comprising a surfactant (such as Tween 80 or Tween 20) and a viscosity-enhancing agent (such as gelatin, alginate, sodium carboxymethylcellulose, etc.). In certain embodiments, the composition is administered subcutaneously. In other embodiments, the composition is administered intravenously. For intravenous delivery, the composition is preferably formulated as microparticles or nanoparticles on average less than about 15 microns, more particularly less than about 10 microns, more particularly less than about 5 microns, and still more particularly less than about 5 microns in average diameter.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated particles. An exemplary formulation for vaginal administration may comprise a bioactive agent that is a contraceptive or an anti-viral, anti-fungal or antibiotic agent.

Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

EXEMPLIFICATION

The invention now being generally described, it will be more readily understood by reference to the following examples, which are included merely for purposes of illustration of certain aspects and embodiments of the present invention, and are not intended to limit the invention.

1. Materials and Methods 1.1 Materials

Poly (D,L-lactic-co-glycolic) (PLGA) (Medisorb High I.V. 54:46) was obtained from Alkermes (Cincinnati, Ohio), and 1,2-diacyl-palmitoyl-glycerol-3-phosphocholine (DPPC) was purchased from Avanti Polar Lipids (Alabaster, Ala.). Dimethyl dioctadecyl ammonium bromide (DDAB), bovine serum albumin (BSA), pig gastric mucin (PGM), and deoxyribonucleic acid (DNA) (sodium salt, from salmon testes) were purchased from Sigma (St. Louis, Mo.) and used without further purification. 2,2,2-Trifluoroethanol (TFE) was purchased from Fluka (Milwaukee, Wis.). Plasmid DNA was extracted from *Escherichia coli* culture (strain DH5a, plasmid p43-c1z1, kindly donated by Dr. Kam Leong, Johns Hopkins University) grown in freshly prepared Luria Bertani (LB) broth supplemented with 100 mg/mL ampicillin (Kodak Chemicals, Rochester, N.Y.) using a Endo-free Qiagen Megaprep (Valencia, Calif.), and subsequently resuspended in sterile, deionized water. The plasmid p43-c1z1 contains the β-galactosidase gene under the human early-intermediate cytomegalovirus (CMV) promoter and also contains a gene for ampicillin resistance. All other solutions and reagents were of analytical grade and used without further purification.

1.2 Formulation of Cationic PLGA Nanoparticles

Particles were prepared by a solvent extraction/precipitation method. PLGA (3 mg/ml) and DDAB (10 mg/ml) were dissolved in TFE separately. Subsequently, 3 ml PLGA solution (9 mg PLGA) and 200 µl of DDAB solution (2 mg DDAB) were combined and added dropwise to 8 mL of filtered distilled water stirring on a magnetic plate. Next, 100 µL of 1 mg/ml salmon testes DNA in distilled water was added to the water/TFE mixture and stirred for 3 hours on a magnetic plate to allow for TFE evaporation. The final formulation was 1.1% DNA to PLGA (wt/wt) and 5% DNA to DDAB (wt/wt). The nanoparticle suspension was then passed through a 1 µm Watman syringe filter (Kent, UK) to remove large impurities and subsequently spun down for 75 minutes at 15,000×g and 4° C. using a Beckman-Coulter Avanti J-25 Centrifuge (Fullerton, Calif.) to pellet nanoparticles. Spin conditions were carefully chosen as to not spin down cationic lipid/DNA particles. PLGA-DDAB/DNA nanoparticles were resuspended in distilled water and lyophilized or used directly for characterization or transport studies.

1.3 Nanoparticle Characterization

The size and surface morphology of the nanoparticles were examined by transmission electron microscopy. Nanoparticles in suspension were adsorbed to carbon-coated ionized formvar grids, negatively stained with 2% uranyl acetate, and observed with Philips 420 transmission electron microscope (Eindhoven, Netherlands).

The size and ζ-potential of the nanoparticles were determined by dynamic light scattering and laser Doppler anemometry, respectively, using a Zetasizer 3000 (Malvern Instruments, Southborough, Mass.). Size measurements were performed at 25° C. at a scattering angle of 90°. Samples were diluted in 150 mM NaCl with or without pig gastric mucin (PGM) (final mucin concentration was 10 mg/ml). ζ-potential measurements were performed according to instrument instructions with samples diluted in 150 mM NaCl with or without PGM (final mucin concentration was 2 mg/ml).

Gel electrophoresis (Mini-sub cell GT, Bio-rad, Hercules, Calif.) was used to verify the binding of DNA to particles and the necessity for cationic surfactants in the DNA adsorption process. Twenty µL of sample was run on an ethidium bromide stained 1.0% agarose gel (70 V for 60 min) in TAE buffer (Tris-Acetate-EDTA).

1.4 Nanoparticle and Naked DNA Transfections with Lac-Z Reporter Gene

Cos-7 cells were obtained from American Type Culture Collection (ATCC, Rockville, Md.) and maintained in Dulbecco's Modified Eagle's Medium (DMEM) (Gibco, BRL) containing 10% fetal bovine serum (Gibco, BRL, Invitrogen Co., Carlsbad, Calif.). Cells seeded at a density of $1.8 \times 10^6$ cells/cm2 on 35-mm 6-well plates were transfected at 50-60% confluency with PLGA-DDAB/DNA nanoparticles or plasmid DNA alone (the concentration in all cases was maintained to yield 2.5 µg DNA per well, or 0.26 µg DNA/cm2). Cells were harvested 48 hours after transfection. β-galactosidase activity and total protein content were assayed using the standard β-galactosidase spectrophotometric assay (Miller, J. Assay of B-Galactosidase, in Experiments in Molecular Genetics; Miller, J. Ed.; Cold Spring Harbor Laboratory: Cold Spring Harbor, 1972; pp 352-355) and the manufacturer's given micro-well protocol for the BCA assay (Pierce Chemical Co., Rockford, Ill.), respectively. Reported values of β-galactosidase expression were normalized to the total protein content per sample well (n=3).

The toxicity of PLGA-DDAB/DNA nanoparticles to Cos-7 cells was assayed using a propidium iodide nucleic acid stain (Molecular Probes; Eugene, Oreg.). Cos-7 cells seeded at $1 \times 10^6$ cells/cm$^2$ were allowed to reach 60% confluency and then incubated with PLGA-DDAB/DNA nanoparticles, naked DNA, or PolyFect/DNA particles and harvested after 48 hours. The PLGA-DDAB/DNA particle volume was adjusted to give final DNA amounts of 1.0, 2.5, and 5.0 μg per well, while naked DNA and PolyFect/DNA concentrations were adjusted to result in a final DNA content of 2.5 μg per well. Harvested cells were resuspended in 500 μg/ml propidium iodide solution, which intercalates with DNA released from necrotic cells. The percentage of dead cells was assayed using flow cytometry. Adsorption and emission maxima for propidium iodide are 535 and 617 nm.

1.5 Formulation and Characterization of Reconstituted Pig Gastric Mucus (PGM)

Mucus was formulated from 60 mg/ml PGM, 3.2 mg/ml DPPC, and 32 mg/ml BSA in sputum buffer (85 mM Na+, 75 mM Cl−, 20 mM Hepes, pH 7.4). Mucus was mixed on a stir plate for 48 hours at 4° C. and stored at −20° C. Sanders et al., Cystic fibrosis sputum: a barrier to the transport of nanospheres. Am J Respir Crit. Care Med 2000, 162, 1905-1911.

Rheological characterization of gastric mucus was performed with a strain controlled cone-and-plate rheometer (ARES-100, Rheometrics, Piscataway, N.J.) as previously described. Tseng et al., Micromechanics and ultrastructure of actin filament networks crosslinked by human fascin: a comparison with alpha-actinin. J Mol Biol 2001, 310, 351-366; Dawson et al, J Biol Chem 2003, 278, 50393-50401. Dynamic tests were performed at 25° C. and buffer evaporation was eliminated using a vapor trap. The time dependent in-phase component of the stress divided by the amplitude of applied oscillatory deformation of fixed frequency, $G'(\omega)$, the out-of-phase component, $G''(\omega$ and the phase angle, $\phi=\tan^{-1}(G''/G')$, is reported. G' and G'' are also commonly referred to as the elastic and viscous moduli, respectively.

Confocal images of particles embedded in reconstituted mucus were captured with an AxioCAM HR camera attached to a Zeiss LSM 510 Meta laser scanning confocal microscope. Mucus was placed in a Bioptechs thermal regulated chamber (Bioptechs, Butler, Pa.) maintained at 37° C. Three-dimensional images were reconstructed using Metamorph software (Universal Imaging Corp., West Chester, Pa.).

1.6 Nanoparticle Transport Rates in PGM with Multiple Particle Tracking (MPT)

Trajectories of fluorescently-labeled carboxylated polystyrene particles (COOH-PS; Molecular Probes; −5 mV ζ-potential at pH 6; 200 nm diameter) and PLGA-DDAB/DNA nanoparticles with condensed salmon testes DNA (35 mV, 196±29 nm diameter) in reconstituted PGM were recorded using a silicon-intensified target camera (VE-1000, Dage-MTI, Michigan, Ind.) mounted on an inverted epifluorescence microscope equipped with 100× oil-immersion objective (numerical aperture 1.3). The trajectories of n=109 COOH-PS and n=120 PLGA-DDAB/DNA particles were tracked in PGM samples contained within a microscope chamber maintained at 37° C.

The centroid of each particle was tracked with 5 nm spatial resolution, determined by tracking the apparent displacements of microspheres immobilized on a glass microslide with a strong adhesive. Apgar et al., Multiple-particle tracking measurements of heterogeneities in solutions of actin filaments and actin bundles. Biophys J 2000, 79, 1095-1106. Nanoparticle motion was tracked in 2-D by following the motion of nanoparticles in the plane of focus. For 2-D displacements to accurately represent 3-D motion, the fluid must be isotropic, but need not be homogeneous. Dawson et al., supra. Images of the microspheres were captured with a custom routine incorporated in the Metamorph software (Universal Imaging Corp.) at a frequency of 30 Hz for 20 s, which gives a temporal resolution of 33 ms. The coordinates of nanoparticle centroids were transformed into families of time-averaged mean squared displacements (MSD), $<\Delta r2(\tau)>=<[x(t+\tau)-x(t)]2+[y(t+\tau)-y(t)]2>$ ($\tau$=time scale or time lag), from which distributions of MSDs and time-dependent particle diffusion coefficients $(D(\tau)=<\Delta r2(\tau)>/4\tau)$ were calculated as previously demonstrated. Tseng et al., Mechanics and multiple-particle tracking microheterogeneity of alpha-actinin-cross-linked actin filament networks. Biophys J 2001, 81, 1643-1656. Diffusion coefficients were normalized with the theoretical diffusion coefficient of 200 nm particles in water as determined by the classical Stokes-Einstein equation.

2. Results and Discussion 2.1 PLGA-DDAB/DNA Nanoparticle

Characterization PLGA-DDAB/DNA nanoparticles with sizes less than 200 nm (FIG. 1: A and B) can be designed to tightly bind DNA with high efficiency (FIG. 1: C). In addition, their small size compared to cationic particles in the micron-range allows them to enter cells, either through non-specific or receptor-mediated endocytosis. Similar to the results that Singh found with cationic microparticles, the transfection efficiency of PLGA-DDAB/DNA nanoparticles was 50-fold higher than that of naked DNA (FIG. 1: D). At the concentration used in the transfection study, PLGA-DDAB/DNA nanoparticles (16.6±6.2% dead cells) were less toxic than PolyFect/DNA particles containing the same amount of DNA (23.9±1.2% dead cells), but more toxic than naked DNA alone (4.7±2.4% dead cells). The toxicity of PLGA-DDAB/DNA nanoparticles showed a dose-dependency with slightly lower particle concentrations (corresponding to 1 μg DNA total, or 2.5-fold lower concentration than used in the transfection study) resulting in background levels of cell toxicity (7.2±0.6% dead cells, not significantly different than naked DNA controls). Singh and coworkers reported that PLGA-DDAB/DNA microparticles caused no acute toxicity with particle doses resulting in the equivalent of 1 mg of DNA per animal (guinea pig). Singh et al. (2000), supra.

Incubation of PLGA-DDAB/DNA nanoparticles in mucus for <30 minutes changed the average particle surface charge from 39±6 mV to −11±7 mV, and the average particle size increased from 196±29 nm to 249±21 nm. The change in size and surface charge of PLGA-DDAB/DNA particles indicated that mucus constituents adsorbed on particle surfaces, leading to a significant increase in particle diameter.

2.2 Rheological Characterization of PGM

The highly viscoelastic properties and gel formation of mucus (phase angle <45°) arise primarily from the high molecular weights and expanded conformations of mucin glycoproteins in aqueous solution. The ability of mucus to undergo gelation is also strongly affected by the concentrations of lipids and macromolecules, which non-covalently interact with mucins promoting the formation of larger mucin fibers that overlap to form dense mucus networks. Quraishi et al., The rheology of nasal mucus: a review. Clin Otolaryngol 1998, 23, 403-413; Rogunova et al., Effects of lipid on the structure and rheology of gels formed by canine submaxillary mucin. Biorheology 1997, 34, 295-308. Physiologically, the high viscoelasticity of mucus gels is maintained to provide a barrier to microbial and particle transport; high elasticity also allows mucus to be engaged by ciliated cells or moved by pulsatory forces as it is cleared from the body. The viscous and elastic properties are properly matched in vivo to achieve appropriate mucus clearance rates. E.g., Quraishi et al., supra.

Figure 2:
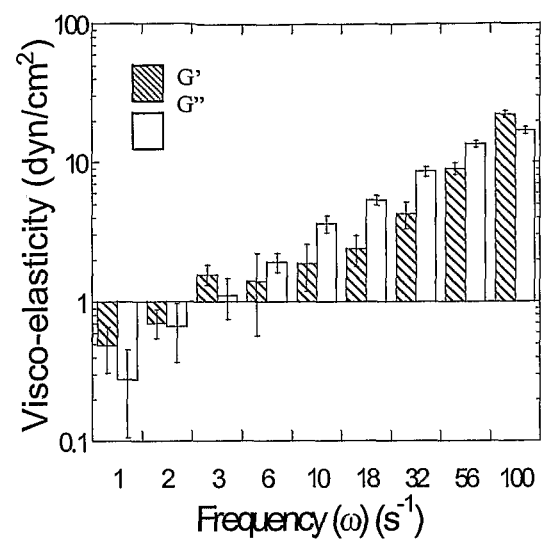
FIG. 2 shows the elastic (G) and viscous (G') moduli of reconstituted pig gastric mucus (n=3). Note that at low frequencies PGM acts more elastic than viscous, with phase angle, $\varnothing=\tan-1$ (G'/G)~30°, but it yields at low frequency (2.5 $s^{-1}$) and the phase angle shifts to $\varnothing$~50°.

The frequency-dependent elastic and viscous moduli were used to characterize the viscoelastic nature of reconstituted pig gastric mucus (PGM) used in this study (FIG. 2). The phase angle of the reconstituted mucus ($\phi=\tan^{-1}(G''/G')=30°$ at $\omega=1$ s−1) showed that the viscosity and elasticity of PGM were matched similarly to physiological mucus. Rogunova et al., supra. At low frequencies, PGM had strong gel-forming properties, but gelation was disrupted at shear rates corresponding to a frequency of $\omega=2.5$ s−1. Reconstituted mucus deforms at lower shear rates than crude mucus. However, particle transport studies are performed on quiescent fluids in this work and, thus, mucus is not subjected to deforming shear conditions.

2.3 PLGA-DDAB/DNA and 200 nm COOH-PS Nanoparticles Embedded in PGM

Following incubation in mucus, the $\zeta$-potential measured for carboxylated polystyrene (COOH-PS) particles (−17.5 mV at pH 6) was close to that for PLGA-DDAB/DNA nanoparticles (−11±7 mV at pH 6), even though the initial $\zeta$-potentials of the two particle types were quite different prior to incubation with mucus (39±6 for PLGA-DDAB/DNA and −5 mV for COOH-PS). This result suggests that mucus components readily adsorb to the surface of each type of particle within minutes of their addition to mucus.

Figure 3:
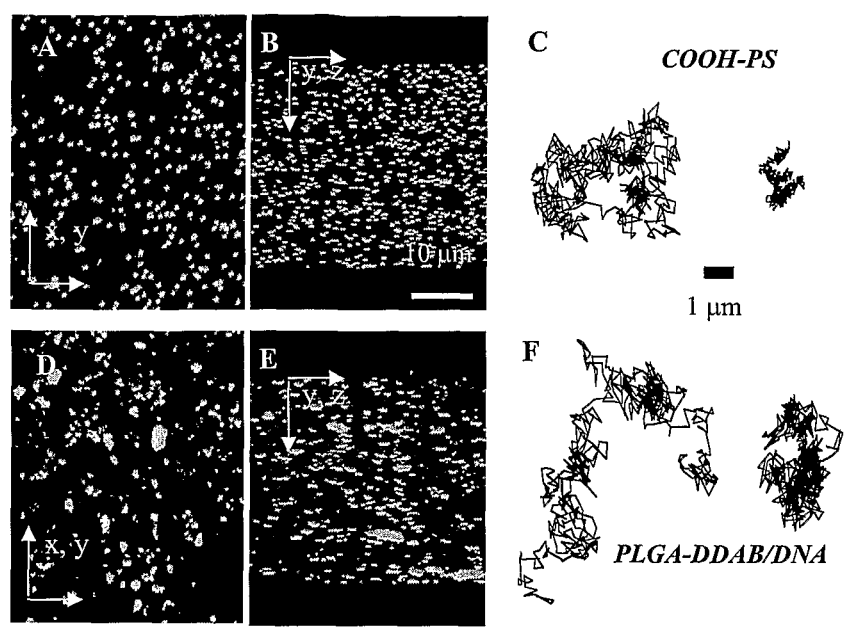
FIG. 3 shows reconstructed 3-D confocal images of fluorescently labeled (A, B) COOH-PS (note the uniform size and distribution) and (D, E) PLGA-DDAB/DNA nanoparticles (particle size is less uniform with aggregates). Diffusive and sub-diffusive 20-s trajectories of (C) COOH-PS and (F) PLGA-DDAB/DNA nanoparticle motion in PGM.

Confocal microscopy was used to collect three-dimensional images of nanoparticles embedded in reconstituted PGM samples (bead solution was ~3% total volume) (FIG. 3: A, B, D, and E). COOH-PS nanoparticles showed reduced aggregation when compared to PLGA-DDAB/DNA nanoparticles, which indicated that PLGA-DDAB/DNA nanoparticles were either adhering as clumps to mucin fibers or aggregating via particle-particle interactions mediated by mucus. Adhesion to mucus may not be surprising since DDAB, which remains on the surface of PLGA-DDAB/DNA nanoparticles, is a cationic surfactant and mucin and other macromolecules found in PGM are strongly anionic. Norris, D., Sinko, P J Appl Polym Sci, 63, 1481-1492. Note that while COOH-PS particles did not appear to aggregate heavily in mucus, they may still be adherent to mucus as individual particles (see next section).

2.4 Nanoparticle Transport Rates Measured with Multiple Particle Tracking (MPT)

The mobility of COOH-PS and PLGA-DDAB/DNA nanoparticles in PGM was tracked in real time in two-dimensions. Suggesting 2-D tracking represents the 3-D mobility of particles assumes that mucus is an isotropic fluid, but not necessarily homogeneous. It is verified with 3-D confocal microscopy that PLGA-DDAB/DNA and COOH-PS particle distributions in mucus are independent of location within the gel in the x, y and z directions (FIG. 3).

Figure 4:
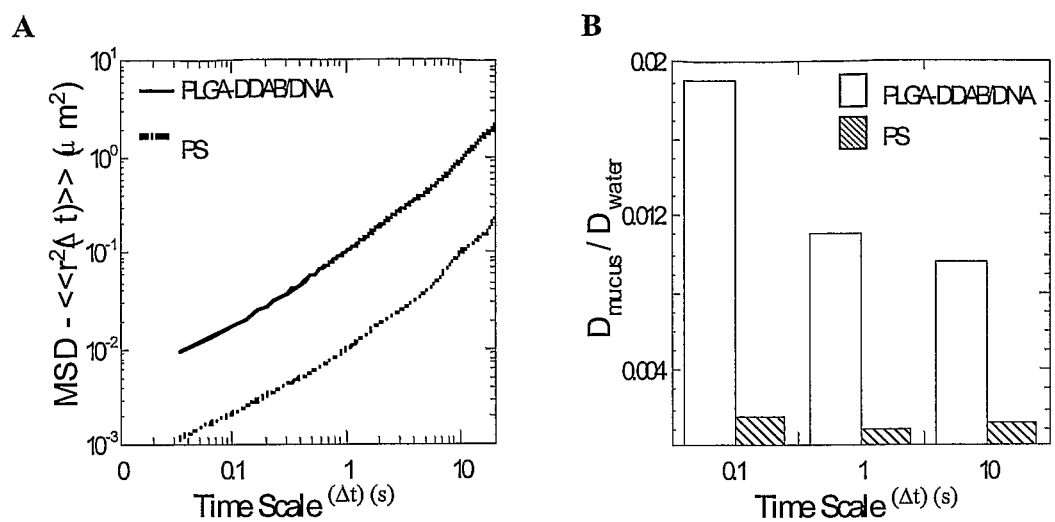
FIG. 4A shows the ensemble mean squared displacement (MSD) of PLGA-DDAB/DNA and COOH-PS nanoparticles in PGM.
FIG. 4B shows the average diffusion coefficients, normalized with the theoretical diffusivity of 200 nm particles in water, of COOH-PS and PLGA-DDAB/DNA nanoparticles.

Twenty-second trajectories of nanoparticle motion in PGM showed that PLGA-DDAB/DNA nanoparticles appeared to be considerably more mobile than COOH-PS nanoparticles (FIG. 3: C and F). Individual particle MSDs were used to determine the average (or "ensemble-average") MSD, allowing the variation in particle transport rates with respect to time to be directly computed. The ensemble MSD of PLGA-DDAB/DNA nanoparticles was 10-fold higher than the ensemble MSD of 200 nm COOH-PS nanoparticles over a range of time scales (FIG. 4A). Furthermore, the ensemble MSD of PLGA-DDAB/DNA nanoparticles had an almost linear dependency on time, indicating that the average transport rate in PGM was dominated by diffusive carriers. Nevertheless, particle motion is severely limited by the viscoelastic nature of PGM, as indicated by the normalized average (or "effective") diffusion coefficients, which are 50-500-fold lower than their theoretical diffusivities in water (FIG. 4B). The normalized diffusion coefficients show that the average particle transport rate decreases slightly with respect to time (FIG. 4B), which would be expected, for example, if a significant fraction of particles underwent sub-diffusive transport (for example, particles adherent to mucus fibers).

Figure 5:
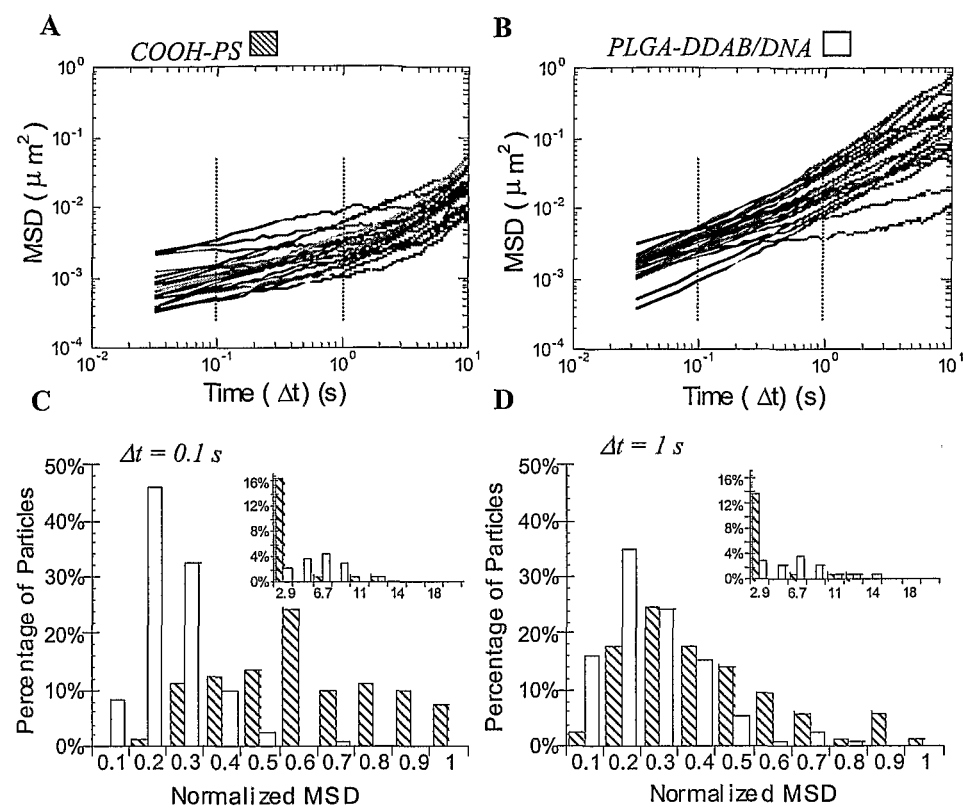
FIG. 5 shows twenty time-dependent particle MSDs for (A) COOH-PS and (B) PLGA-DDAB/DNA nanoparticles, randomly selected (n=109 and 120, respectively). The distribution of MSDs for COOH-PS (hatched bars) and PLGA-DDAB/DNA (open bars) particles, normalized with their respective ensemble averaged MSD, at (C) Δt=0.1 s and (D) Δt=1 s indicate that the majority of particles have MSDs less than the average. Note that a small percentage of faster particles largely affects the average rate of transport (see insets), especially at small time scales when many particles are moving with more sub-diffusive transport rates.

The observation that PLGA-DDAB/DNA particles moved faster on average than COOH-PS particles was somewhat counterintuitive since PLGA-DDAB/DNA nanoparticle aggregation was expected to reduce their transport rates. Therefore, to further elucidate the mode and rate of particle transport in PGM, we examined the distributions of individual particle MSDs (FIG. 5). The mode of transport of each individual particle was determined by the slope of the particle MSD versus time on a log-log scale. A slope <1 indicated that transport was sub-diffusive, or hindered, while a slope ~1 indicated that transport was diffusive. For time scales <1 s, COOH-PS nanoparticle MSDs were primarily sub-diffusive (FIG. 5: A), indicating that a majority of these particles (101 of 109, or 93%, at time-scales between 0.1-1 s) are transiently adherent to mucus or are temporarily trapped within cages formed by mucus fibers. In contrast, considerably more PLGA-DDAB/DNA nanoparticles had diffusive MSDs at earlier time scales (FIG. 5: B), with only 78% (94 of 120) undergoing sub-diffusive transport at time scales between 0.1-1 s. Therefore, although a considerable fraction of PLGA-DDAB/DNA particles appear to aggregate in PGM, a significantly higher percentage of PLGA-DDAB/DNA particles (22%) undergo diffusive transport at early time scales compared to COOH-PS particles (7%).

To quantify the degree of heterogeneity in particle transport rates, the distributions of the individual MSDs of COOH-PS and PLGA-DDAB/DNA nanoparticles at time scales of $\Delta t=0.1$ s and 1 s were normalized by their respective ensemble average MSDs (FIG. 5: C and D). In general, the mean MSD of each particle type was significantly smaller than the ensemble average MSD, indicating that a small percentage (~10%) of the particles contributed significantly to the average rate of transport. At early time scales ($\Delta t=0.1$ s), when transport of COOH-PS nanoparticles was primarily sub-diffusive, the mean of the MSD was only 2-fold lower than the average; at larger time scales ($\Delta t=1$ s), the mean was nearly 5-fold lower than the average. In contrast, for all time scales, PLGA-DDAB/DNA nanoparticles had mean transport rates that were 5-fold lower than the average. This result provided further evidence that a high percentage of COOH-PS nanoparticles were either transiently adherent to mucus or temporarily trapped in microscopic cages in PGM over short time scales (thereby leading to a more homogeneous distribution of transport rates). Given time, some COOH-PS particles could resume diffusion by desorbing or escaping their sub-diffusive cages (leading to an increase in the heterogeneity of the particle transport rates). On the other hand, a higher number of PLGA-DDAB/DNA nanoparticles had diffusive transport rates at short time scales, leading to high heterogeneity in particle transport rates, but fewer changed their mode of transport over time, which was apparent in the similarities of the mean MSD at time scales of $\Delta t=0.1$ s and 1 s. This result suggests that, following the adhesion of a fraction of the PLGA-DDAB/DNA particles, a significant percentage of the remaining particles were able to undergo unrestricted diffusive transport. Heterogeneities in particle transport rates may be important in assessing the efficiency of particles in traversing the mucosal barrier since gene delivery may only require a small percentage of gene carriers to reach target epithelial cells. Hanes et al., supra.

There are several possible explanations for the more rapid transport of the slightly aggregated (and thus, larger) PLGA-DDAB/DNA particles compared to COOH-PS particles. For example, Olmstead and coworkers (Olmstead et al., supra) demonstrated that herpes simplex virus (HSV) particles adhere to mucin fibers found in cervical mucus, causing the fibers to collapse into coil-like structures and inducing the formation of larger pores around the condensed mucus. The rearrangement of the mucus network promoted more rapid local transport of HSV particles. Similarly, the observed PLGA-DDAB/DNA particle aggregates with mucus may have led to larger pores that promoted more rapid transport of PLGA-DDAB/DNA particles compared to COOH-PS particles. This hypothesis is supported indirectly by the fact that a considerably higher percentage of PLGA-DDAB/DNA nanoparticles (8.5%) exhibited an MSD greater than 5-fold of their ensemble average MSD compared to only 2.9% for COOH-PS nanoparticles, each at a time scale of 0.1 s (7.7% versus 3.9% at a time scale of 1 s for PLGA-DDAB/DNA versus COOH-PS, respectively).

A second possible explanation for the increased transport rates of PLGA-DDAB/DNA nanoparticles compared to the slightly smaller COOH-PS nanoparticles may be related to the difference in surface chemistries of the two particle types. PLGA-DDAB/DNA nanoparticle surfaces are coated with DNA, making them relatively hydrophilic compared to COOH-PS nanoparticles. Mucus is composed of a dense network of fibers that are relatively hydrophobic compared to the solution contained within the network pores. Therefore, it is possible that the fraction of PLGA-DDAB/DNA nanoparticles that do not interact electrostatically with negatively charged mucin glycoproteins are capable of enhanced transport in the hydrophilic mucus pores compared to COOH-PS particles, a larger fraction of which may adhere as single particles to the mucus network. This hypothesis is supported by the finding that a larger fraction of COOH-PS particles undergo sub-diffusive, or hindered, transport compared to PLGA-DDAB/DNA particles (FIG. 5). The fact that each particle type appears to adsorb mucus components (as indicated by the decrease in $\zeta$-potential for each particle upon incubation in mucus) presumably makes the particle surfaces more similar. If the entire surface is coated by mucus components, then the differences in initial surface chemistries may not be important, thus favoring the former hypothesis.

2.5 Conclusions Based on Sections 2.1-2.4

Multiple particle tracking (MPT) was used to study transport rates of individual gene carriers in gastric mucus. Advantages of MPT include the ability to study individual particle transport and distributions of transport rates, as well as their contributions to the average or "bulk" properties, in complex biological environments. Dawson et al., J. Biol. Chem., 2003, 278: 50393-50401; Suh et al., Efficient active transport of gene nanocarriers to the cell nucleus. Proc Natl Acad Sci USA 2003, 100, 3878-3882. Transport rates of cationic nanoparticles made from PLGA-DDAB/DNA in PGM were measured and their transport rates were much higher (~10-fold) than that of slightly smaller COOH-PS nanoparticles. It is possible for larger particles (such as the PLGA-DDAB/DNA particles) to move more rapidly through a porous media than smaller particles by, for example, altering the pore network of the mucus or by spending less time on average either physically trapped within cages formed by elastic mucus fibers or, perhaps more likely, adherent to mucus fibers. Regardless, rapid transport through mucus and the ability to transfect cells make PLGA-DDAB/DNA particles interesting for further in vitro and in vivo testing as gene delivery agents.

2.6 Surface Modification of Different Core Particles with PEG.

PEG moieties were conjugated onto the surface of PEI/DNA nanocomplexes at different N/P ratios and PEG concentrations. Transport rates of PEI/DNA complexes with N/P ratio of 20 (unmodified) and modified with 10% PEG concentration were quantified using multiple particle tracking techniques.

PEG moieties were non-specifically adsorbed to the surface of 500-nm polystyrene particles using a standard adsorption protocol accessible through Polysciences, Inc. (March 1999, Technical Data Sheet 238E; 0304RevD, Technical Data Sheet 238F). The transport rates of control particles and surface modified polystyrene particles (modified with PEG 3000, PLL, or BSA) were measured with multiple particle tracking techniques. One dimensional diffusivity of unmodified polystyrene particles was also determined with time-lapsed confocal microscopy.

Liposomal formulations of DOTAP:DOPE were also modified to include PEG. DOPE:PEG-2000 was combined with a cationic lipid-based transfection reagent, DOTAP:DOPE, and a fluorescent lipid, NBD:DOPE, at ratios of 1:48:1, respectively. Briefly, cationic lipids were combined and dissolved in 1:1 chloroform/methanol mixture (50 mM lipid composition) and rotary evaporated. The liposomes were resuspended by shaking the film in 20 mM Hepes buffer at 4° C. for 24 hours, sonicating in 30 second pulses for 10 intervals, and filtering solutions with 0.4 µm Whatman filter. Liposomes were complexed with DNA at a 1:1 ratio, final DNA concentration was 25 µg/ml DNA. Reduced adhesion of particles in mucus was assayed by confocal microscopy and laser Doppler anemometry.

Particles with surface chemistries that favor interaction with mucus, including more hydrophobic or highly-charged particles, can be used as mucoadhesive particles to target drugs, contraceptives, or other products to mucus or biomacromolecules that are adhesive with the modified particle surface.

2.7 Effects of Surface Modification of Particles with PEG on the Rate of Particle Transport in Mucus Quantified with Real-Time Multiple Particle Tracking.

Quantitative investigations of the transport of drug or gene carrying particles are currently poorly documented. MPT is a powerful method for studying particle transport rates since this method allows us to simultaneously measure the transport rates of hundreds of individual particles in real time. Particles that can effectively transport through mucus must be able to move through the mucus mesh with minimal interactions, e.g., by being preferably small and resistant to adsorption to mucus.

2.8 Previous Application of Multiple Particle Tracking in Assessing Particle Transport and Adhesion in Mucus.

To improve the design of gene carriers, transport rates in CF mucus were correlated with physicochemical properties of standard particles, including size and surface properties. Multiple particle tracking (MPT) was used to determine the transport rates of polystyrene particles with different diameters in CF mucus. Dawson et al., J. Biol. Chem., (2003) 278:50393-50401. As the diameter of the particles increased from 100-500 nm, the mean squared displacements and effective diffusivities decreased by nearly 10-fold. The Stokes-Einstein equation was used to determine the microviscosity of the mucus, which is the viscosity encountered by a particle transporting through the fluid, from the effective diffusivity of 100, 200, and 500 nm particles. The microviscosities that the 100-500 nm particles encountered were 10-100 times lower than the macroviscosities of CF mucus as measured by cone and plate rheometry. This difference is simply explained by the fact that particles only transport in the relatively low viscosity pores of the CF mucus mesh, whereas macrorheology takes into account the entire mesh. Since the microviscosities have a larger effect on the rate of gene carrier transport, MPT was used to probe the effects of physiochemical properties on the microviscosities they encounter in mucus.

After surface modification of polystyrene, polysebacic acid, DOTAP:DOPE and polyethylenimine particles with PEG particles this technique was applied to assessing the effects of surface-modification on transport rates in mucus.

Figure 6:
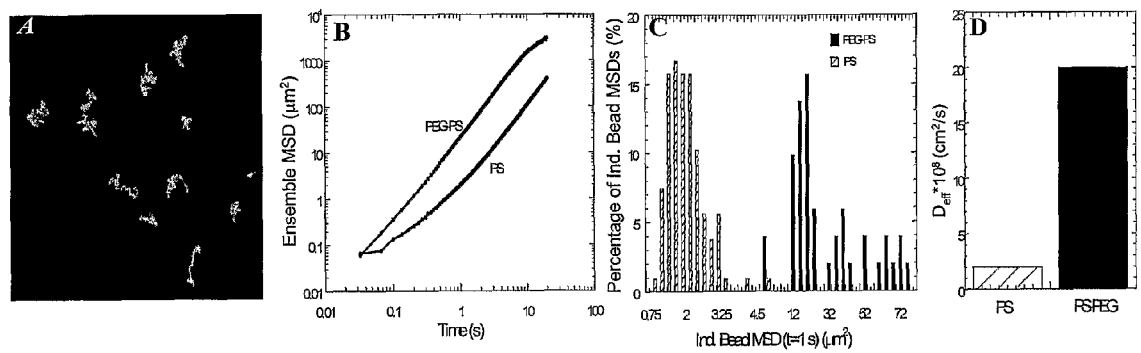
FIG. 6 shows multiple particle tracking (MPT) used to quantify effects of surface modification by PEG adsorption on polystyrene particle transport rates in bovine cervical mucus. (A) Tracking the MSDs from particle trajectories with real-time MPT and epifluorescence video microscopy. (B) MSDs of PS particles vs. PEG-modified PS particles showing that PEG-modified particles move one to two orders of magnitude more quickly through mucus. (C) The distribution of the individual bead MSDs at t=1 s further demonstrates the vastly improved transport rates of PEG-modified particles. (D) Effective diffusivities (t=1 s) of PS particles vs. PEG-modified PS particles.

The effect of surface modification with PEG on transport rates of polystyrene particles in mucus were quantified with multiple particle tracking (FIG. 6). This data shows that PEG modification can greatly enhance the diffusion of PS particles into mucus (FIG. 6).

Figure 7:
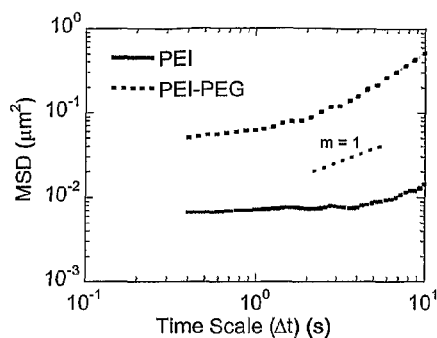
FIG. 7 shows MPT data used to quantify effects of surface modification by PEG of PEI/DNA particle transport rates in mucus. (A) MSDs of PEI particles vs. PEG-modified PEI particles showing that PEG-modified particles move much more quickly through mucus. (B) The distribution of the individual bead MSDs at t=1 s further demonstrates the vastly improved transport rates of PEG-modified particles with a decreased percentage of adhesive particles (reduced % of particles in the $0-6.7\times10^{-3}$ μm² bin). (C) The percentage of non-adhesive (mobile) particles defined as particles with MSD $<0.67\times10^{-3}$ μm².
Figure 7:
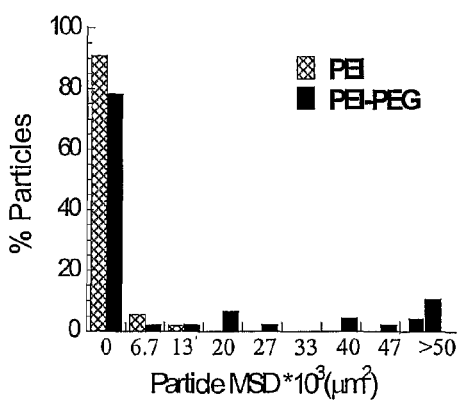
Figure 7:
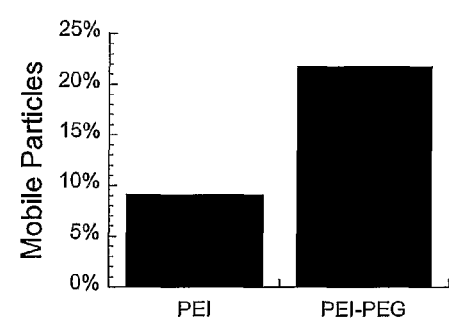

The effect of surface modification with PEG (10% PEG) on polyethylenimine particles (N/P ratio of 20) transport rates in CF mucus was quantified with multiple particle tracking (FIG. 7). This data shows that PEG modification can greatly enhance the diffusion of PEI gene carriers into mucus (FIG. 7).

2.9 Determining the Mean Squared Displacement, Diffusion Coefficient, and Mode of Transport of Particles as Measured by Multiple Particle Tracking (MPT).

Images of particles were acquired as described (Apgar et al., Biophys. J. (2000) 79:1095-1106) using a SIT camera (VE-1000 Dage-MTI, Michigan City, Ind.) mounted on an inverted epifluorescence microscope maintained at 37° C. and equipped with a 100-× magnification, 1.3 numerical aperture, oil-immersion lens (Nikon, Melville, N.Y.). These images were analyzed using a custom subroutine incorporated to the software Metamorph (Universal Imaging Corp., West Chester, Pa.). The displacements of the centroids of individual microspheres were simultaneously tracked in the focal plane of the microscope for 20 s at a rate of 30 Hz, as many times as necessary to monitor a total of ~100 particles for each tested specimen. Software was available to track hundreds of particles simultaneously, but the density of the microspheres was adjusted to limit the number of probe particles to 10-30 per field of view in order to reduce potential correlated interactions between neighboring particles. The spatial resolution, which was evaluated by tracking the apparent displacement of latex beads firmly tethered to the coverslip, was ~5 nm. From the trajectories of the microspheres centroids, individual time-lag-averaged mean squared displacements (MSD), $<\Delta r2(t)>$, were computed (Palmer et al., Biophys. J., (1999) 76:1063-1071), from which time-lag-dependent MSD distributions and distribution of the diffusion coefficient ($D=<\Delta r2(t)>/4t$), were generated. These distributions were normalized by the time-lag-averaged, ensemble-averaged MSD and subsequently analyzed by computing median, standard deviation, and skewness, statistical parameters that describe the heterogeneity of transport through the samples. Gene vectors can be tracked a minimum distance of 2-5 μm from the coverslip, which should eliminate the effects of capillary forces between gene vectors and the coverslip. Since the physiochemical properties, including size, surface charge, and composition, are not independent, the MPT data can be normalized using MPT data collected from standard polystyrene particles with known size and surface charge.

2.10 Effects of Surface Modification of Particles with PEG on the Diffusivity of Particles in Mucus as Observed with Time-Lapsed Confocal Microscopy.

Confocal microscopy was used to measure the apparent diffusional velocity of particles or gene carriers in a mucus slab. With this technique, particles are added to the surface of a mucus slab, and the motion of the particle front into the fluid is assayed by determining the depth of penetration of the particles (in two-dimensional (x,y) image) into the fluid (third dimension (z)). The diffusivity is calculated by one-dimensional diffusion model ($\Delta z2$/total time).

Figure 8:
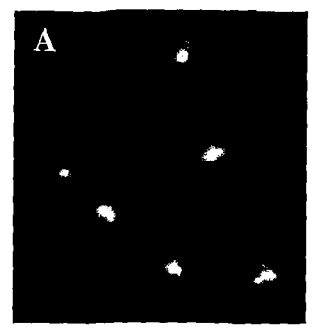
FIG. 8 shows the mobility of PEI/YFP and PEI-PEG/YFP (10% PEG) complexes determined by 4-D confocal microscopy. (A) Confocal image of PEG-PEI/DNA nanocomplexes following the addition of avidin, NeutraLite Texas Red conjugate. The PEI is labeled with Oregon Green (both dyes from Molecular Probes). Colocalization of red (avidin) and green (PEI/DNA) implies successful conjugation of Biotin-PEG to PEI/DNA nanocomplexes. (B) Schematic view of the 4-D confocal microscopy that was used for PEI, PEI-PEG, PS, PLGA-DDAB/DNA, PSA-PEG, etc.: Fluorescent particles were deposited on the surface of CF sputum, and allowed to diffuse randomly through the specimen. (C) Mobility of PLGA-DDAB/DNA in synthetic mucus modeling lung mucus determined by 4-D confocal microscopy.
Figure 8:
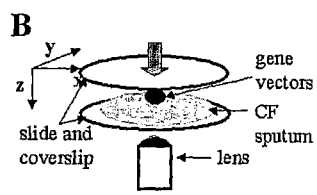
Figure 8:

Over a 30 min period PEI/YFP (yellow fluorescent protein DNA) complexes added to the surface of a sputum slab remained in the same x-y plane (slice thickness was 0.37 μm) while PEI-PEG (10%)/YFP complexes translocated over several planes (distance ~1 μm) (FIG. 8). The measured velocity of PEI-PEG/YFP particles was 330 nm/min in 30 min.

Velocity of unmodified PEI/DNA carriers was too small to measure. The effective diffusion coefficient of PEG-modified PEI/DNA complexes, obtained by assuming Fickian diffusion, was $2.7 \times 10^{-41} m^2/s$.

One-dimensional diffusivities of PLGA-DDAB/DNA, pSA-PEG, and PS particles in synthetic mucus formulated to model lung mucus were measured using time lapsed confocal microscopy. The diffusivity of PS particles in synthetic mucus was $5.3 \times 10^{-5} \mu m^2/s$ since particles moved 0.4 μm in 50 minutes. The diffusivity of PLGA-DDAB/DNA particles was $2 \times 10^{-3} \mu m^2/s$ since particles moved 2.48 μm in 50 minutes. The diffusivity of pSA-PEG in mucus was $2 \times 10^{-2} \mu m/s$ since particles moved 10.78 μm in 86 minutes (the slice thickness was increased to ensure that the motion was captured). pSA-PEG particles diffused more rapidly than PLGA-DDAB/DNA particles which diffused more rapidly than PS. Increased mobility of pSA-PEG is evidence of the increased mobility of PEG-coated particles.

2.11 Determination of the One-Dimensional Diffusivity of Particles in Mucus or Other Fluids Using Laser Scanning Confocal Microscopy.

Confocal images of gene vectors in CF sputum are captured with the high performance cooled digital camera AxioCAM HR, attached to a Zeiss LSM 510 Meta laser scanning confocal microscope. The LSM 510 Meta is well-suited for time-lapsed 3-dimensional imaging since the microscope is completely motorized and fully automated through LSM software. Subroutines, which allow us to repeat the experimental conditions including the thickness of the z-slice, laser intensity, and time and bleaching intervals, were developed for each application including the FRAP, 4-D mobility, and avidity assays. By allowing the LSM software to control the course of microscopy experiments we are able to repeat experimental conditions with great precision.

Figure 13:
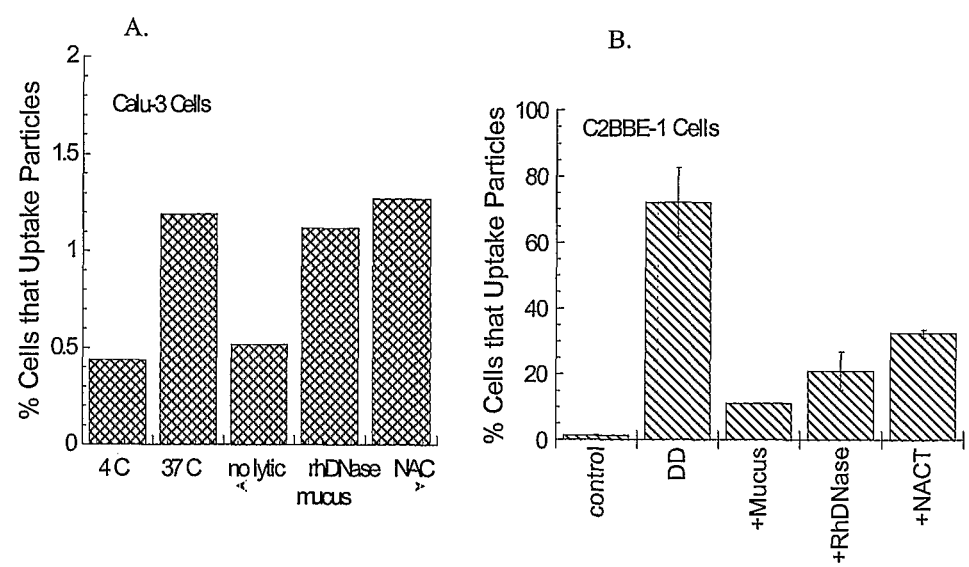
FIG. 13 shows the uptake of (A) 200 nm PS particles in Calu-3 lung cells and (B) cationic DOTAP:DOPE liposomes in C2BBE-1 colon cells is increased by the addition of mucolytic agents.

Gene vectors suspended in solution (10 μl) applied to the surface of a CF sputum sample on a Biophetic cover slide, which is imaged with a LSM 510 Meta confocal—an inverted light microscope (thus vectors are moving into the plane of focus). The cover slide was placed in the Bioptechs thermal regulated chamber and allowed to heat up and equilibrate for approximately 30 minutes prior to imaging. Slice thickness is optimized to increase the depth of focus (~30 μm), so gene vectors that move rapidly can be imaged over a long period of time (90 minutes). Four-dimensional (x, y, z, and t) images of CF sputum slab are collected over a 30-90-minute time period with a time-interval of 5 minutes (FIG. 13). This technique allows us to track the motion of gene vectors and determine an effective velocity and 1D diffusion coefficient of gene vectors in CF sputum—before and after the addition of mucolytic agents. Although this technique does not allow high temporal resolution as seen in MPT, it is an excellent complement for MPT in that it gives us a method of estimating the long-range mobility of gene vectors. This method was also used to focus on immobile beads and to determine changes in mobility after the addition of mucolytic agents.

2.12 Effects of Surface-Modification with PEG on the Adhesion of Particles with Mucus.

Mucus adsorption to particle surface results in large changes in the size and zeta-potential of particles not modified with PEG. Dawson et al., Biotechnol. Prog. 2004, 20:851-857. PEG-modified particles had more neutral surface charge and underwent less extreme changes in surface charge indicating that less mucus adsorbs to the particle surfaces suggesting particles are less adhesive to mucus.

2.13 Effects of Addition of Targeting Ligand on the Uptake and Transfection of Surface-Modified Particles by Lung or Gut Cells.

Figure 10:
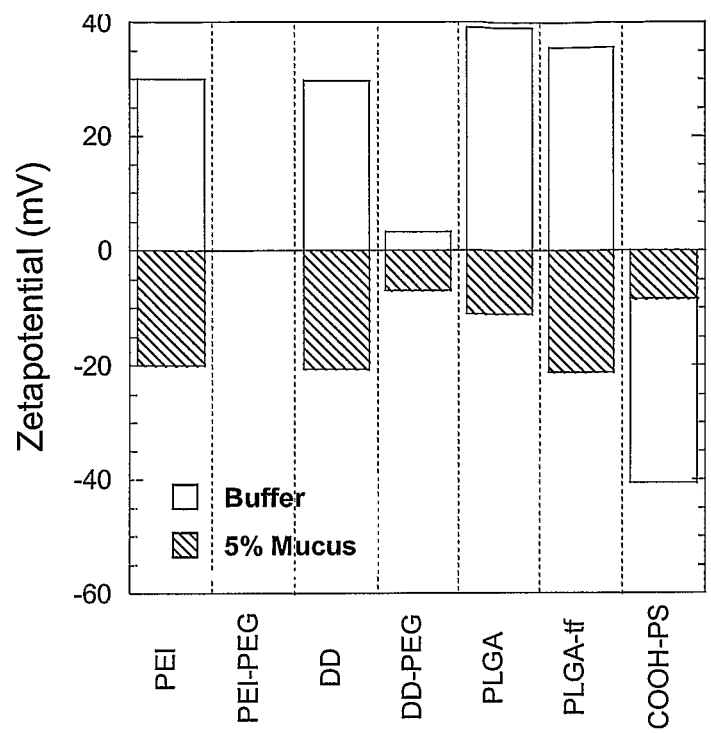
FIG. 10 shows zetapotentials of nanoparticle gene carriers in 150 mM NaCl and in 1:20 pig gastric mucus/150 mM NaCl. Notation and specific information: An N/P ratio of 20 was used for PEI complexes, DD (DOTAP:DOPE), PLGA (PLGA-DDAB/DNA), PLGA-tf (PLGA-DDAB/DNA with Apo-Transferrin). The addition of transferrin to the particle surface is understood not to significantly change the surface charge of PLGA-DDAB/DNA particles.
Figure 11:
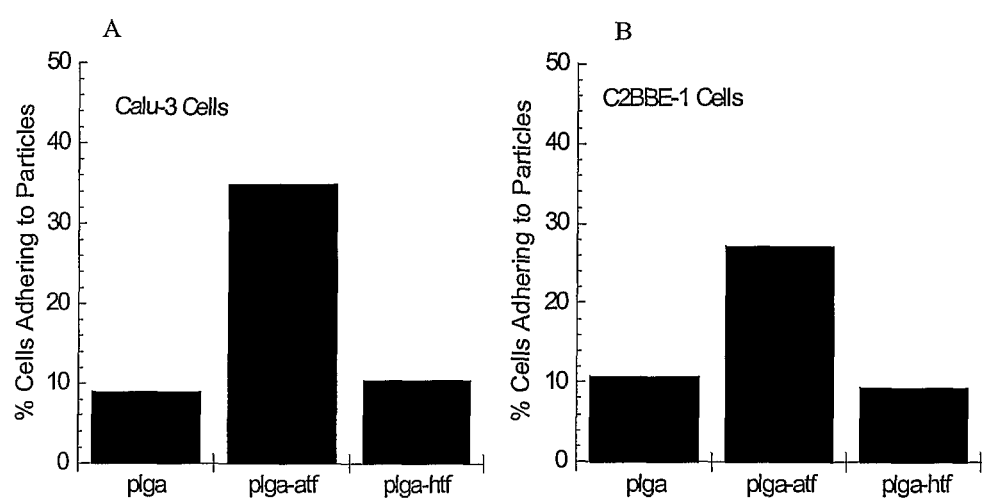
FIG. 11 shows 4° C. Adhesion of PLGA-DDAB/DNA NPs modified with apo-transferrin or holo-transferrin to (A) lung and (B) gut cells.
Figure 12:
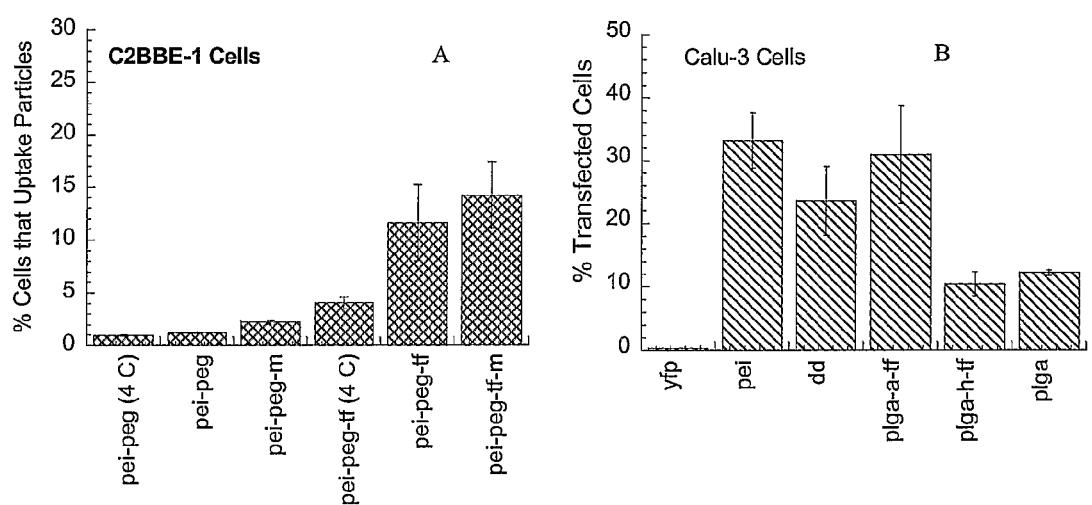
FIG. 12 shows that (A) PEI-PEG and (Note: 4° C. is a control and indicates adhesion and not uptake since endocytosis requires cells to be at 37° C., m indicates that particles were added to cells with 10% mucus on the surface) (B) PLGA-DDAB/DNA nanoparticles (Note: dd is DOTAP:DOPE, a-tf is apo-transferrin and h-tf is holo-transferrin) were modified with avidin-transferrin and apo-transferrin, respectively. The ability for colon cells to internalize fluorescently-labeled PEI-PEG particles and for PLGA-DDAB/DNA particles to transfect lung cells and express yellow fluorescent protein (YFP) was determined by flow cytometry.

Particles modified with PEG are more neutrally charged (FIG. 10) than cationic particles and do not interact non-specifically with cells (FIGS. 11 and 12). To improve the interactions with cells, a cell-specific targeting ligand was added to the particles (FIG. 11). The addition of transferrin to the particle surface improved the interaction with cells used in the studies since they are immortalized from cancer tissues, which have been known to use transferrin-specificity to steal the body's nutrients and direct them to cancerous cells or tissues. The methods used were modifications of standard assays using flow cytometry to quantify the uptake of fluorescent particles or transfection with fluorescent protein. PEI-PEG-Tf was internalized by gut cells more efficiently than PEI-PEG and had high levels of uptake even in the presence of mucus (FIG. 12: A). PLGA-DDAB/DNA with apo-Tf transfected cells more efficiently than particles without Tf or particles with other types of Tf. In addition, the transfection efficiency of C was as good as that of PEI (N/P—20) gene carriers and DOTAP:DOPE liposomes. Since the other carriers are currently used in clinical trials and numerous studies, PLGA-DDAB/DNA with apo-Tf may also be good candidates for clinical studies.

2.14 Addition of Mucolytic Agents to Mucus Prior to Particle Administration Increases Uptake of Particles.

Using concentrations of mucolytic agents used in transport experiments, the ability of mucus to increase particle uptake into cells was tested. Addition of mucolytic agents increased uptake of PS particles (FIG. 13: A) in Calu-3 (lung) cells and uptake of cationic liposomes (DOTAP:DOPE) (FIG. 14: B) into C2BBE-1 (gut) cells.

2.15 Effect of Surface-Modification of PS Particles with BSA on the Rate of Particle Transport in Bovine Cervical Mucus.

Figure 14:
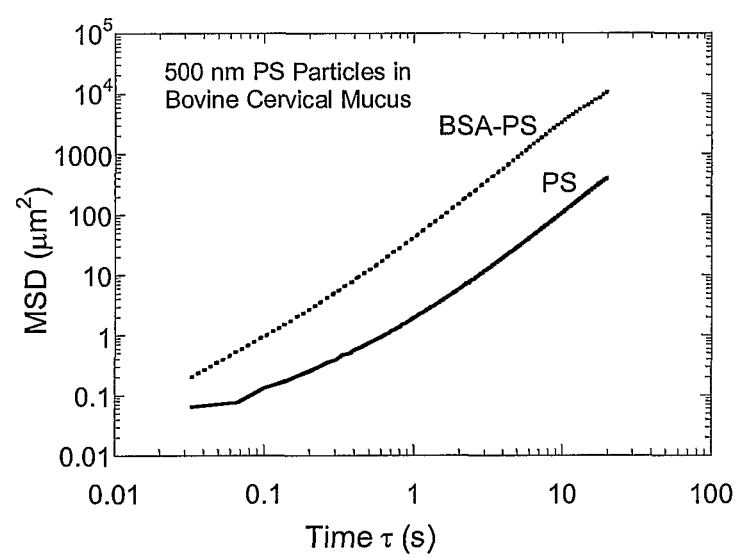
FIG. 14 shows the effect of surface-modification of PS particles with BSA on the rate of particle transport in bovine cervical mucus. PS particles are 500-nm in diameter and the transport rates is assayed by multiple particle tracking (shown is the ensemble average MSD of 60-80 particles for each).
Figure 15:
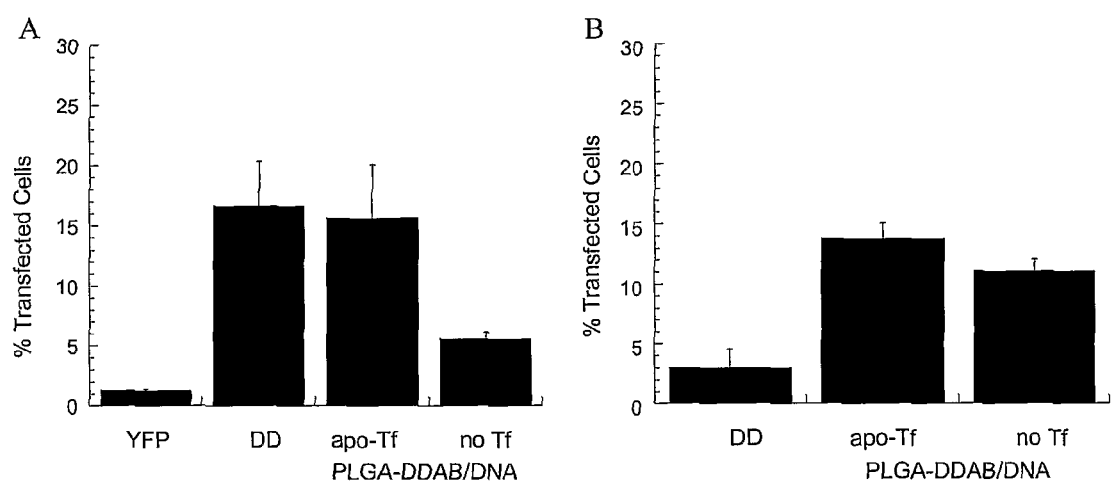
FIG. 15 shows the transfection efficiency of PLGA-DDAB/DNA nanoparticles (modified with apo- and holo-transferrin) in C2BBE-1 colon cells as compared to the transfection efficiency of DOTAP/DOPE nanoparticles. PLGA-DDAB/DNA nanoparticles (esp. with transferring) transfect mucus-covered cells more efficiently than DOTAP:DOPE. (A) Without mucus (B) With Mucus.

As shown in FIG. 14, BSA-coated particles move more rapidly in mucus than PS, suggesting that coating particle surface with a protein or polymer, such as PAA, may also increase transport in mucus.

References

All publications and patents mentioned herein, are hereby incorporated by reference in their entirety as if each individual publication or patent was specifically and individually indicated to be incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A polymeric particle comprising a pharmaceutically acceptable polymer core, a bioactive agent, and a surface-altering agent disposed on the surface of the core, wherein the surface-altering agent enhances the average rate at which the particle moves in mucus by at least 5-fold compared to the same particle except without a surface-altering agent disposed on the surface,
    wherein the surface-altering agent reduces the overall charge on the surface of the polymeric particle and enhances the hydrophilicity of the surface of the polymeric particle compared to the same particle except without a surface-altering agent disposed on the surface,
    wherein the surface-altering agent comprises polyethylene glycol having a molecular weight of about 2-3kDa, and
    wherein the polymeric particle is less than about 1 micron in diameter.

2. The polymeric particle of claim 1, wherein the bioactive agent is encapsulated in the polymer core.

3. The polymeric particle of claim 1, wherein the pharmaceutically acceptable polymer core comprises a polymer selected from the group consisting of: a poly (D,L-lactic-co-glycolic) acid, polyethylenimine, dioleyltrimethylammoniumpropane/dioleyl -sn-glycerolphosphoethanolamine, poly (anhydrides), and a polymer formed from clinically approved monomers.

4. The polymeric particle of claim 1, wherein the bioactive agent is a therapeutic agent or an imaging agent.

5. The polymeric particle of claim 4, wherein the therapeutic agent is a DNA, an RNA, a small molecule, a peptidomimetic, or a protein.

6. The polymeric particle of claim 1, wherein the bioactive agent is a diagnostic agent.

7. The polymeric particle of claim 4, wherein the imaging agent further comprises a detectable label.

8. The polymeric particle of claim 1 further comprising an adjuvant.

9. The polymeric particle of claim 1, wherein the polymeric particle is less than 200nm in diameter.

10. The polymeric particle of claim 1, wherein the polymeric particle passes through mucus at a greater rate than a polystyrene particle of the same size.

11. A pharmaceutical composition comprising the polymeric particle of claim 1 and a pharmaceutically acceptable carrier.

12. An inhaler comprising the polymeric particle of claim 1.

13. The polymeric particle of claim 1, wherein the average rate at which the particle moves in mucus is at least 10-fold greater than the rate of the same particle except without the surface-altering agent disposed on the surface.

14. The polymeric particle of claim 1, wherein the polyethylene glycol has a molecular weight of about 2 kDa.

15. The polymeric particle of claim 1, wherein the polyethylene glycol has a molecular weight of about 3 kDa.

16. The polymeric particle of claim 1, wherein the polyethylene glycol is attached to polyethyleneimine (PEI).

17. The polymeric particle of claim 1, wherein the polymeric particle is less than about 500 nm in diameter.

18. A particle comprising a pharmaceutically acceptable core, a bioactive agent, and a surface-altering agent disposed on the surface of the core, wherein the surface-altering agent enhances the average rate at which the particle moves in mucus by at least 5-fold compared to the same particle except without a surface-altering agent disposed on the surface,
    wherein the surface-altering agent reduces the overall charge on the surface of the particle and enhances the hydrophilicity of the surface of the particle compared to the same particle except without a surface-altering agent disposed on the surface,
    wherein the surface-altering agent comprises polyethylene glycol having a molecular weight of about 2-3 kDa, and
    wherein the particle is less than about 1 micron in diameter.

19. The particle of claim 18, wherein the bioactive agent is encapsulated in the core.

20. The particle of claim 18, wherein the average rate at which the particle moves in mucus is at least 10-fold greater than the rate of the same particle except without the surface-altering agent disposed on the surface.

21. The particle of claim 18, wherein the bioactive agent is a DNA, a RNA, a small molecule, a peptidometic, or a protein.

22. The particle of claim 18, wherein the bioactive agent comprises a siRNA.

23. The particle of claim 18, wherein the polyethylene glycol has a molecular weight of about 2 kDa.

24. The particle of claim 18, wherein the polyethylene glycol has a molecular weight of about 3 kDa.

25. The particle of claim 18, wherein the polyethylene glycol is attached to polyethyleneimine (PEI).

26. The particle of claim 18, wherein the particle is less than about 500nm in diameter.

27. The particle of claim 18, wherein the particle is less than about 200nm in diameter.

28. A pharmaceutical composition comprising the particle of claim 18 and a pharmaceutically acceptable carrier.

* * * * *